United States Patent
Riley et al.

(10) Patent No.: US 9,994,818 B2
(45) Date of Patent: Jun. 12, 2018

(54) ICOS CRITICALLY REGULATES THE EXPANSION AND FUNCTION OF INFLAMMATORY HUMAN TH17 CELLS

(71) Applicant: The Trustees of the University of Pennsylvania, Philadelphia, PA (US)

(72) Inventors: James L. Riley, Downingtown, PA (US); Chrystal Paulos, Philadelphia, PA (US); Carl H. June, Merion Station, PA (US); Bruce L. Levine, Cherry Hill, NJ (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 276 days.

(21) Appl. No.: 14/823,281

(22) Filed: Aug. 11, 2015

(65) Prior Publication Data

US 2015/0342994 A1 Dec. 3, 2015

Related U.S. Application Data

(62) Division of application No. 13/576,249, filed as application No. PCT/US2011/023744 on Feb. 4, 2011, now Pat. No. 9,133,436.

(60) Provisional application No. 61/301,506, filed on Feb. 4, 2010.

(51) Int. Cl.
| | |
|---|---|
| *A61K 35/26* | (2015.01) |
| *C12N 5/0783* | (2010.01) |
| *A61K 35/17* | (2015.01) |
| *A61K 39/00* | (2006.01) |

(52) U.S. Cl.
CPC ............ *C12N 5/0637* (2013.01); *A61K 35/17* (2013.01); *C12N 5/0636* (2013.01); *A61K 2039/5158* (2013.01); *A61K 2039/57* (2013.01); *C12N 2501/2301* (2013.01); *C12N 2501/2302* (2013.01); *C12N 2501/2306* (2013.01); *C12N 2501/2321* (2013.01); *C12N 2501/2323* (2013.01); *C12N 2501/51* (2013.01); *C12N 2501/515* (2013.01); *C12N 2501/599* (2013.01)

(58) Field of Classification Search
None
See application file for complete search history.

(56) References Cited

U.S. PATENT DOCUMENTS

| | | | |
|---|---|---|---|
| 7,722,872 B2 | 5/2010 | Kroczek | |
| 2002/0102658 A1 | 8/2002 | Tsuji et al. | |
| 2004/0005298 A1 | 1/2004 | Bonyhadi et al. | |
| 2004/0005557 A1* | 1/2004 | Padigaru | C07K 14/47 435/6.18 |
| 2004/0054158 A1* | 3/2004 | Ling | C07K 14/70532 536/23.5 |
| 2004/0110290 A1 | 6/2004 | June et al. | |
| 2006/0034810 A1 | 2/2006 | Riley et al. | |
| 2006/0140944 A1* | 6/2006 | Yoshinaga | C07K 14/705 424/144.1 |
| 2008/0254137 A1 | 10/2008 | Raymond et al. | |
| 2008/0286283 A1 | 11/2008 | Kroczek | |
| 2010/0028450 A1* | 2/2010 | Vasu | A61K 39/385 424/491 |
| 2010/0203056 A1* | 8/2010 | Irving | A61K 31/7068 424/139.1 |
| 2012/0251556 A1* | 10/2012 | Allison | A61K 39/3955 424/173.1 |

FOREIGN PATENT DOCUMENTS

| | | |
|---|---|---|
| WO | WO 2009/155477 | 12/2009 |
| WO | WO 2010/099205 | 9/2010 |

OTHER PUBLICATIONS

Nurieva et al. (2007) Nature 448, 480-483.*
Dong et al. J Autoimmun. 2003; 21:255-260.*
Korn et al. PNAS, 2008; 105: 18460-18465.*
Kimura et al. Eur. J. Immunol. 2010; 40: 1830-1835.*
Paulos et al. Sci Transl Med. (2010) 2(55); 55ra78, 14 pages.*
Chung et al. (2009) Immunity 30, 576-587.*
Watanabe et al. J Immunol 2008; 180: 5222-5234.*
Conti et al., 2015; Cent Eur J Immunol. 40(3): 380-386.*
Liappas et al., 2015; BioMed Research International, vol. 2015, Article ID 416480, 9 pages.*
Ochs et al., 2009; J Allergy Clin Immunol. 123(5): 977-985.*
Singh et al., Autoimmunity Reviews (2014) 13: 1174-1181. (Year: 2014).*
Deng et al., Hybridoma and Hybridomics (2004) 23: 176-182. (Year: 2004).*
Australian Patent Application No. 2014224141—Patent Examination Report No. 1 dated Dec. 23, 2015.
Australian Patent Application No. 2014224141—Patent Examination Report No. 2 dated Jul. 28, 2016.
European Patent Application No. 11740423.6—Official Communication dated Sep. 26, 2016.

(Continued)

*Primary Examiner* — Ilia I Ouspenski

(74) *Attorney, Agent, or Firm* — Saul Ewing Arnstein & Lehr LLP; Kathryn Doyle

(57) ABSTRACT

The invention includes compositions and methods for generating and expanding therapeutic Th17 cells. The invention includes contacting T cells with a composition comprising a first agent that is capable of providing a primary activation signal to T cells and a second agent that is capable of activating ICOS on T cells in the presence of Th-17 polarizing agents.

5 Claims, 23 Drawing Sheets

(56) References Cited

OTHER PUBLICATIONS

Canadian Patent Application No. 2,791,975—Office Action dated Feb. 3, 2017.
Annunziato et al., "The phenotype of human Th17 cells and their precursors, the cytokines that mediate their differentiation and the role of Th17 cells in inflammation." 2008, International Immunology, 20(11):1361-1368.
Axtell et al., "T helper type 1 and 17 cells determine efficacy of interferon-beta in multiple sclerosis and experimental encephalomyelitis." 2010 Nat. Med. 16:406-412.
Bauquet et al., "The costimulatory molecule ICOS regulates the expression of c-Maf and IL-21 in the development of follicular T helper cells and TH-17 cells." 2009 Nat. Immunol. 10:167-175.
Bernard et al., "Costimulatory receptors in jawed vertebrates: conserved CD28, odd CTLA4 and multiple BTLAs." 2007 Immunol. 31:255-271.
Bossaller et al., "ICOS deficiency is associated with a severe reduction of CXCR5+CD4 germinal center Th cells." 2006 J. Immunol. 177:4927-4932.
Burmeister et al., "ICOS controls the pool size of effector-memory and regulatory T cells." 2008 J. Immunol. 180:774-782.
Canderan, "T helper 17 T cells do good for cancer immunotherapy." 2009, Immunity 31(5):787-798 (abstract).
Carpenito et al., "Control of large, established tumor xenografts with genetically retargeted human T cells containing CD28 and CD137 domains." 2009 Proc. Natl. Acad. Sci. U.S.A. 106:3360-3365.
Cosmi et al., "Human interleukin 17-producing cells originate from a CD161+CD4+ T cell precursor." 2008 J. Exp. Med. 205:1903-1916.
Duhen et al., "Production of interleukin 22 but not interleukin 17 by a subset of human skin-homing memory T cells." 2009 Nat. Immunol. 10:857-863.
Gross et al., "Identification and distribution of the costimulatory receptor CD28 in the mouse." 1992 J. Immunol. 149:380-388.
Homey et al., "Up-regulation of macrophage inflammatory protein-3 alpha/CCL20 and CC chemokine receptor 6 in psoriasis." 2000 J. Immunol. 164:6621-6632.
Huang Z., "Structural chemistry and therapeutic intervention of protein-protein interactions in immune response, human immunodeficiency virus entry, and apoptosis." Pharmacology and Therapeutics, 200, 86:201-215.
Hutloff et al., "ICOS is an inducible T-cell co-stimulator structurally and functionally related to CD28." 1999 Nature 397:263-266.
Ito et al., "Two functional subsets of FOXP3+ regulatory T cells in human thymus and periphery." 2008 Immunity 28:870-880.
Kehrl et al., "Production of transforming growth factor beta by human T lymphocytes and its potential role in the regulation of T cell growth." J. Exp. Medicine, 1986, 163:1037-1050.
King et al., "T follicular helper (TFH) cells in normal and dysregulated immune responses." 2008 Annu. Rev. Immunol. 26:741-766.
Lyke et al., "Serum levels of the proinflammatory cytokines interleukin-1 beta (IL-1beta), IL-6, IL-8, IL-10, tumor necrosis factor alpha, and IL-12(p70) in Malian children with severe Plasmodium falciparum malaria and matched uncomplicated malaria or healthy controls." Infection and Immunity, 2004, 72:5630-5637.
Manel et al., "The differentiation of human T(H)-17 cells requires transforming growth factor-beta and induction of the nuclear receptor RORgammat." Nature Immunology, 2008, 9:641-649.
Martin-Orozco et al., "T helper 17 cells promote cytotoxic T cell activation in tumor immunity." 2009 Immunity 31: 787-798.
Maus et al., "Ex vivo expansion of polyclonal and antigen-specific cytotoxic T lymphocytes by artificial APCs expressing ligands for the T-cell receptor, CD28 and 4-1BB." 2002 Nat. Biotechnol. 20:143-148.
Muranski et al., "Tumor-specific Th17-polarized cells eradicate large established melanoma." 2008 Blood 112:362-373.
Murphy et al., "Effector T cell plasticity: flexibility in the face of changing circumstances." 2010 Nat. Immunol. 11:674-680.
Park et al., "A distinct lineage of CD4 T cells regulates tissue inflammation by producing interleukin 17." 2005 Nat. Immunol. 6:1133-1141.
Parry et al., "CD28 and inducible costimulatory protein Src homology 2 binding domains show distinct regulation of phosphatidylinositol 3-kinase, Bcl-xL, and IL-2 expression in primary human CD4 T lymphocytes." 2009 J. Immunol. 171:166-174.
Riley et al., "ICOS costimulation requires IL-2 and can be prevented by CTLA-4 engagement." 2001 J Immunol 166(8):4943-4948.
Riley et al., "The CD28 family: a T-cell rheostat for therapeutic control of T-cell activation." 2005 Blood 105:13-21.
Schaefer et al., "ICOS promotes IL-17 synthesis in colonic intraepithelial lymphocytes in IL-10 -/- mice" 2009, Journal of Leukocyte Biology 87(2):301-308.
Suhoski et al., "Engineering artificial antigen-presenting cells to express a diverse array of co-stimulatory molecules." 2007 Mol. Ther. 15:981-988.
Tafuri et al., "ICOS is essential for effective T-helper-cell responses." 2001 Nature 409:105-109.
Takahashi et al., "Impaired CD4 and CD8 effector function and decreased memory T cell populations in ICOS-deficient patients." 2009 J. Immunol. 182:5515-5527.
Turka et al., "CD28 is an inducible T cell surface antigen that transduces a proliferative signal in CD3+ mature thymocytes." 1990 J. Immunol. 144:1646-1653.
Vojdani et al., "The Role of Th17 in Neuroimmune Disorders: Target for CAM Therapy. Part I." 2011 Evid Based Complement Alternat Med 2011:927294. Epub Jun. 16, 2011.
Yang et al., "IL-21 and TGF-beta are required for differentiation of human T(H)17 cells." 2008 Nature 454:350-352.
Yu et al., "Roquin represses autoimmunity by limiting inducible T-cell co-stimulator messenger RNA." 2007 Nature 450:299-303.
Zou et al., "T(H)17 cells in tumour immunity and immunotherapy." 2010 Nat. Rev. Immunol. 10:248-256.

\* cited by examiner

ICOS CRITICALLY REGULATES THE EXPANSION AND FUNCTION OF INFLAMMATORY HUMAN TH17 CELLS

CROSS-REFERENCE TO RELATED APPLICATION

This application is a divisional of U.S. patent application Ser. No. 13/576,249 filed on Nov. 29, 2012, which is a U.S. national phase application filed under 35 U.S.C. § 371 claiming benefit to International Patent Application No. PCT/US11/23744, filed on Feb. 4, 2011, which is entitled to priority under 35 U.S.C. § 119(e) to U.S. Provisional Patent Application No. 61/301,506, filed on Feb. 4, 2010, each of which application is hereby incorporated herein by reference in its entirety.

STATEMENT REGARDING FEDERALLY SPONSORED RESEARCH OR DEVELOPMENT

This invention was made with government support under grant numbers NIH 5R01CA105216, NIH 1R01CA120409, NIH 5P01CA066726 and NIH R01AI057838 awarded by the National Institutes of Health. The Government therefore has certain rights in this invention.

BACKGROUND OF THE INVENTION

CD4+ T cells are important in regulating immunity to pathogens, allergic responses, asthma, and immunity to self or tumor tissues (Zhu et al., 2010 Annu Rev. Immunol. 28:445-489; Muranski et al., 2009 N. P. Restifo, Curr. Opin. Immunol. 21:200-208; Zhu et al., 2008 Blood 112:1557-1569). Depending on the microenvironmental cues present, naïve CD4+ T cells may differentiate into one of several T helper (TH) cell lineages, including TH1, TH2, Th17, TH22, and regulatory T (Treg) cells (O'Shea et al., 2010 Science 327:1098-1102; Murphy et al., 2010 Nat. Immunol. 11:674-680). TH1 and TH2 cells are effector cells that express T-bet and GATA-3, respectively (Zhu et al., 2010 Annu Rev. Immunol. 28:445-489). In contrast, Treg cells suppress effector T cell functions and are essential for regulating autoimmune responses (Tang et al., 2006 Immunol. Rev. 212:217-237), and the recently described TH22 cells secrete interleukin-22 (IL-22) and might be a subset of skin-homing cells responsible for inflammation (Duhen et al., 2009 Nat. Immunol. 10:857-863; Trifari et al., 2009 Nat. Immunol. 10:864-871). Th17 cells augment host defense, have a major role in mucosal immunity, enhance a number of autoimmune diseases, and release cytokines, including IL-17A and IL-17F (Korn et al., 2009 Annu Rev. Immunol. 27:485-517). The contribution of Th17 cells to tumor immunity varies, showing the potential for both antitumorigenic and protumorigenic activity (Zou et al., 2010 Nat. Rev. Immunol. 10:248-256). Therefore, identification of the mechanisms that control Th17 responses is essential to understand tumor immunity. The functions of cytokines (for example, transforming growth factor-β (TGF-β), IL-6, IL-1b, IL-21, and IL-23) and transcription factors (such as RORC2 and RORa) in human Th17 cell development are distinct from TH1 and TH2 effector cells (Zhou et al., 2009 Curr. Opin. Immunol. 21:146-152; Manel et al., 2008 Nat. Immunol. 9:641-649; Yang et al., 2008 Nature 454:350-352; Volpe et al., 2008 Nat. Immunol. 9:650-657). Further, natural agonists for the aryl hydrocarbon receptor (AHR) augment murine Th17 cell differentiation (Veldhoen et al., 2009 J. Exp. Med. 206:43-49). However, the specific costimulatory pathways that may influence Th17 generation and stability remain to be elucidated.

Antigen-specific and antigen-nonspecific costimulatory signals from antigen-presenting cells (APCs) are necessary for the activation, differentiation, and function of T lymphocytes (Greenwald et al., 2005 Annu Rev. Immunol. 23:515-548). CD28 is considered to be the primary co-signaling molecule on CD4+ T cells because of its early expression, and it is often used to generate IL-17-producing lymphocytes (Manel et al., 2008 Nat. Immunol. 9:641-649; Yang et al., 2008 Nature 454:350-352; Volpe et al., 2008 Nat. Immunol. 9:650-657; Acosta-Rodriguez et al., 2007 Nat. Immunol. 8:942-949; Acosta-Rodriguez et al., 2007 Nat. Immunol. 8:639-646; Wilson et al., 2007 Nat. Immunol. 8:950-957). However, in addition to CD28, signaling via the inducible costimulator (ICOS, also called CD278) is required for optimal cytokine secretion, because both molecules are essential for optimal IL-17A secretion by murine Th17 cells (Park et al., 2005 Nat. Immunol. 6:1133-1141). Recent findings in murine models have revealed that ICOS amplifies Th17 responses by inducing the expression of the transcription factor c-MAF and therefore transactivating IL-21 production (Bauquet et al., 2009 Nat. Immunol. 10:167-175).

Although both CD28 and ICOS are important for the generation of murine Th17 cells, their particular roles in regulating key genes in human Th17 cells remain to be identified. The present invention satisfies this need in the art.

SUMMARY OF THE INVENTION

The invention provides a composition comprising a first agent that is capable of providing a primary activation signal to a T cell and a second agent that is capable of activating ICOS on said T cell.

In one embodiment, the comprising is a solid phase surface. In another embodiment, the composition is a human cell line. In yet another embodiment, the human cell line is selected from the group consisting of K562, U937, 721.221, T2, and C1R cells.

In one embodiment, the cell is genetically modified to express a human Fcγ receptor. In another embodiment, the Fcγ receptor is selected from the group consisting of CD32, CD64, and any combination thereof.

In one embodiment, the first agent binds CD3 or a component of the TCR/CD3 complex. In another embodiment, the second agent is anti-ICOS antibody or ICOS-L.

In another embodiment, the cell is further genetically modified to express said second agent. In another embodiment, the cell is further modified to express a cytokine. In yet another embodiment, the cytokine is selected from the group consisting of IL-1β, IL-2, IL-6, IL-23 and any combination thereof.

In another embodiment, the cell is further modified to express an inhibitory molecule that inhibits a cytokine that interferes with Th17 differentiation process. Preferably, the cytokine that interferes with Th17 differentiation process is selected from the group consisting of IFNγ, IL-4, and any combination thereof.

The present invention also includes a method for activating or stimulating a population of T cells. The method comprises: 1) providing a population of cells wherein at least a portion thereof comprises T cells; 2) contacting the population of cells with a composition comprising a first agent that is capable of providing a primary activation signal to the T cells and a second agent that is capable of activating ICOS on said T cells.

In one embodiment, contacting the population of cells with a composition comprising a first agent that is capable of providing a primary activation signal to the T cells and a second agent that is capable of activating ICOS on the T cells is in the presence of a Th-17 polarizing agent.

In one embodiment, the Th-17 polarizing agent is selected from the group consisting of IL-1β, IL-6, neutralizing anti-IFNγ, anti-IL-4, and any combination thereof.

In one embodiment, the T cells are CD4+ T cells.

In another embodiment, the T cells are umbilical cord T cells.

In another embodiment, the T cells are peripheral T cells.

In one embodiment, the T cells secrete heightened levels of IL-17A, IL-17F and CCL20 after at least one, two, three, four, five, six, seven, or eight rounds of stimulation as compared with cells costimulated with CD28.

In one embodiment, the T cells secrete elevate levels of IFNγ, TNFα and IL-21 as compared with CD28 costimulation.

In another embodiment, the T cells are contacted with an antigen. In one embodiment, the antigen is a tumor antigen.

The present invention includes a method of immunotherapy comprising administering an ICOS stimulated T cell to a patient in need thereof. In one embodiment, the ICOS stimulated T cell has been contacted with a first agent that is capable of providing a primary activation signal to T cells and a second agent that is capable of activating ICOS on T cells in the presence of a Th-17 polarizing agent.

In one embodiment, the Th-17 polarizing agent is selected from the group consisting of IL-1β, IL-6, neutralizing anti-IFNγ, anti-IL-4, and any combination thereof.

In one embodiment, the first agent binds CD3 or a component of the TCR/CD3 complex. In another embodiment, the second agent is anti-ICOS antibody or ICOS-L.

In one embodiment, the Th17 has been contacted with an antigen.

The present invention also provides a population of cultured expanded Th17 cells exhibiting antitumor activity, wherein the antitumor activity is retained long term and wherein the cells are expanded to a number sufficient for effective therapy in a mammal.

The invention also provides a method of regulating a Th17 cell in a mammal. The method comprises administering to the mammal an effective amount of composition comprising a first agent that is capable of providing a primary activation signal to a T cell and a second agent that is capable of activating ICOS on said T cell.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A through 1C, is a series of images depicting distinct expression and function of ICOS and CD28 on human CD4+ T cell subsets. FIG. 1A is an image demonstrating that the expression of ICOS and CD28 costimulatory molecules was assessed on resting human peripheral blood CD4+ T cell subsets, consisting of CXCR3+CCR4−CCR6+ $T_H1$, CCR4+CXCR3−CCR6− $T_H2$, CCR4+CCR6+ Th17, CD25+CD127loFoxP3+ Treg, and CXCR5+CD45RO+ TFH cells. FIG. 1B is an image depicting flow cytometric quantification of ICOS and CD28 on different subsets from several normal donors (n=7). Horizontal bars indicate mean; ns=not significant. FIG. 1C is an image depicting cytokines IL-2 (i), IL-4 (ii), IFN-γ (iii), IL-10 (iv), IL-22 (v), IL-17A (vi), IL-17F (vii), CCL20 (viii), and IL-21 (ix) secreted from various sorted cells activated with antibodies to CD3/CD28 or CD3/ICOS beads and measured on day 3 by ELISA. Statistics were corrected for multiple comparisons with the ANOVA Scheffé test. TFH=follicular helper T.

FIGS. 2A through 2G, is a series of images demonstrating that ICOS augments cytokine production by human Th17 cells. FIG. 2A is an image demonstrating that IL-17F production was assessed by peripheral blood CD4+ T cells differentiated to a Th17 phenotype with Th17-polarizing conditions (IL-6, IL-1b, IL-23, neutralizing IFN-γ, and neutralizing IL-4 antibodies in serum containing TGF-β, a cytokine required for inducing Th17 differentiation) and activated with either aAPCs expressing CD86, CD80, CD70, ICOSL, OX40L, or 4-1BBL or with beads bearing antibodies to CD3 and CD28 on day 3 by ELISA. FIG. 2B is an image demonstrating that IL-17F production was assessed by peripheral blood CD4+ T cells cultured with or without Th17-polarizing conditions and activated with aAPC engineered to express ICOSL or with beads bearing antibodies to CD3/ICOS on day 3. FIG. 2C to 2G depicts measurements of (C) IL-17F, (D) IL-17A, (E) IL-2, (F) IL-22, and (G) IL-10 secretion or expression by Th17-polarized CD4+ T cells activated with beads bearing antibodies to CD3, CD28, and/or ICOS on day 3 using ELISA or reverse transcription PCR (RT-PCR).

FIGS. 3A through 3G, is a series of images demonstrating that ICOS is critical for the expansion of human Th17 cells. FIGS. 3A and 3B depict the frequency and absolute number, respectively of CCR4+CCR6+CD4+ T cells over time assessed by flow cytometry from peripheral blood CD4+ T cells cultured in Th17-polarizing conditions and activated with antibodies to CD3/CD28 or CD3/ICOS beads. FIG. 3C is an image demonstrating that CD27 and CD62L expression was measured on day 10 on these cells with flow cytometry. FIG. 3D demonstrate that on the days indicated, CD28- or ICOS-engaged Th17-polarized CD4+ T cells were stimulated with PMA-ionomycin and the frequency of cells secreting IL-17A and IFN-γ was assessed via flow cytometry. FIG. 3E is an image demonstrating that the frequency of CD28- or ICOS-engaged Th17-polarized cells coproducing IL-17A and/or IFN-γ was determined at the end of their primary expansion (ranging from days 9 to 14) in several different normal donors (n=8). FIGS. 3F and 3G demonstrate expression of RORC2 and T-bet, respectively, in these treated cells measured using RT-PCR on days 3 and 10.

FIGS. 4A through 4F, is a series of image demonstrating that ICOS drives rapid Th17 cell differentiation from naïve UCB CD4+ T cells. FIGS. 4A through 4C, is a series of image demonstrating that UCB CD45RA+CD25−CD4+ T cells were cultured with Th17-polarizing conditions and expanded with antibodies to CD3/CD28, CD3/ICOS, or CD3/CD28/ICOS beads. Starting on day 3, IL-2 (50 IU/ml) was added to the cultures. Cultures were stimulated with PMA-ionomycin (IONO) and the intracellular expression of IL-17A, IFN-γ, IL-2, and TNF-α and the extracellular expression of IL-23R and CD161 were assessed on day 11. Cells from FIG. 4A to FIG. 4C were reactivated with antibodies to CD3-coupled beads bearing antibodies to CD28 and/or ICOS. FIGS. 4D to 4F demonstrate that cultures were restimulated with PMA-ionomycin and the intracellular expression of IL-17A, IFN-γ, IL-2, and TNF-α and the extracellular expression of IL-23R and CD161 were assessed on day 18.

FIGS. 5A through 5L, is a series of image demonstrating that CD28 and ICOS differentially regulate c-MAF, RORC2, and T-bet expression in UCB Th17 cells. UCB CD4+ T cells were cultured in Th17-polarizing conditions and expanded with antibodies to CD3/CD28 or CD3/ICOS beads. IL-2 (50 IU/ml) was added on day 3. FIGS. 5A and 5B demonstrate that on day 5, mRNA expression of c-MAF and IL-21 in CD28- or ICOS-stimulated cells was measured by RT-PCR. FIG. 5C demonstrate that on day 5, IL-17F production in CD28-stimulated cells cultured with exogenous IL-21 and IL-2 neutralization was measured by ELISA. FIGS. 5D through 5L demonstrate that on the days indicated, RORC2, T-bet, FoxP3, AHR, IL-22, IL-10, and IL-17A production in CD28- or ICOS- stimulated cells was measured by flow cytometry and RT-PCR.

FIGS. 6A through 6E, is a series of images demonstrating that human Th17 cells originate from ICOS+CD161+CD4+ T cell precursors. FIG. 6A demonstrates that CD45RA, CD31, CD127, CD62L, and CD27 expression was assessed on ICOS+CD161+CD4+ and ICOS−CD161+CD4+ T cells from the UCB via flow cytometry. FIG. 6B is an image demonstrating that IL-17F, CCL20, IFN-γ, IL-4, IL-22, and IL-10 secretion by sorted ICOS+CD161+CD4+ and ICOS−CD161+CD4+ T cells cultured with Th17-polarizing conditions and expanded with antibodies to CD3/CD28 or CD3/ICOS beads was assessed on day 4 by ELISA. FIG. 6C is an image depicting the frequency and absolute number of CD161+ cells cultured with Th17-polarizing conditions and expanded with antibodies to CD3/CD28- or CD3/ICOS-coated beads that were determined on day 4 or on the days indicated, respectively. FIG. 6D is an image depicting RORC2, IL-23R, AHR, and FoxP3 mRNA expression in sorted ICOS+CD161+CD4+ and ICOS−CD161+CD4+ T cells cultured with Th17-polarizing conditions and expanded with antibodies to CD3/CD28- or CD3/ICOS-coated beads that were assessed on day 7 by RT-PCR. FIG. 6E is an image demonstrating that on day 7, ICOS+CD161+CD4+ and ICOS−CD161+CD4+ T cells cultured in media alone or in TH1-, TH2-, Th17-, and Treg-polarizing conditions and expanded with antibodies to CD3/CD28- or CD3/ICOS-coated beads were then stimulated with PMA-ionomycin, and IL-17A secretion was assessed by flow cytometry.

FIGS. 7A through 7F, is a series of images demonstrating that ICOS augments T cell-mediated tumor immunity. As shown schematically, human CD4+ and CD8+ T cells were stimulated with antibodies to CD3/CD28 or CD3/ICOS beads and cultured with or without Th17-polarizing conditions. One day later, bead-activated T cells were genetically redirected with a CAR that binds mesothelin. After their primary expansion, the genetically redirected cells (two administrations, 8×10$^6$ cells total) were infused into mice bearing a large human mesothelin (M108) tumor pre-established for 61 days (n=8 mice per group). FIGS. 7A through 7D demonstrate that tumor growth was measured in mice infused with genetically redirected cells expanded with the ICOS or CD28 signal with or without Th17-polarizing conditions. Tumor growth was analyzed with a linear mixed-effects model and by applying a conservative Bonferroni correction approach (mean±SEM). FIG. 7E demonstrates that redirected T cells were isolated from the mouse spleens (on day 43) and cultured with irradiated aAPCs bearing mesothelin. IL-17A and IFN-γ secretion was analyzed by flow cytometry 24 hours later. FIG. 7F demonstrates that the absolute number of CD4+ and CD8+ T cells was determined in the blood and spleen on days 21 and 43, respectively.

FIGS. 13A through 13D, is a series of images demonstrating that ICOS+CD161+CD4+ T cells are imprinted as Th17 cells. CD4+ and ICOS+CD161+CD4+ T cells from UCB were sorted and cultured in various polarizing conditions as indicated. The frequency of IFN-γ+(FIG. 13A), IL-4+(FIG. 13B), IL-17 A+(FIG. 13C) or FoxP3+(FIG. 13D) cells was measured after their primary expansion with anti-CD3 beads bearing anti-CD28 or anti-ICOS antibodies. As a control, companion control cultures of bulk UCB CD4 T cells were stimulated with antiCD3/CD28 beads. Cytokines and FoxP3 were measured by flow cytometry or ELISA on day 7 of culture post-stimulation with PMA/ionomycin.

DETAILED DESCRIPTION OF THE INVENTION

Figure 1:
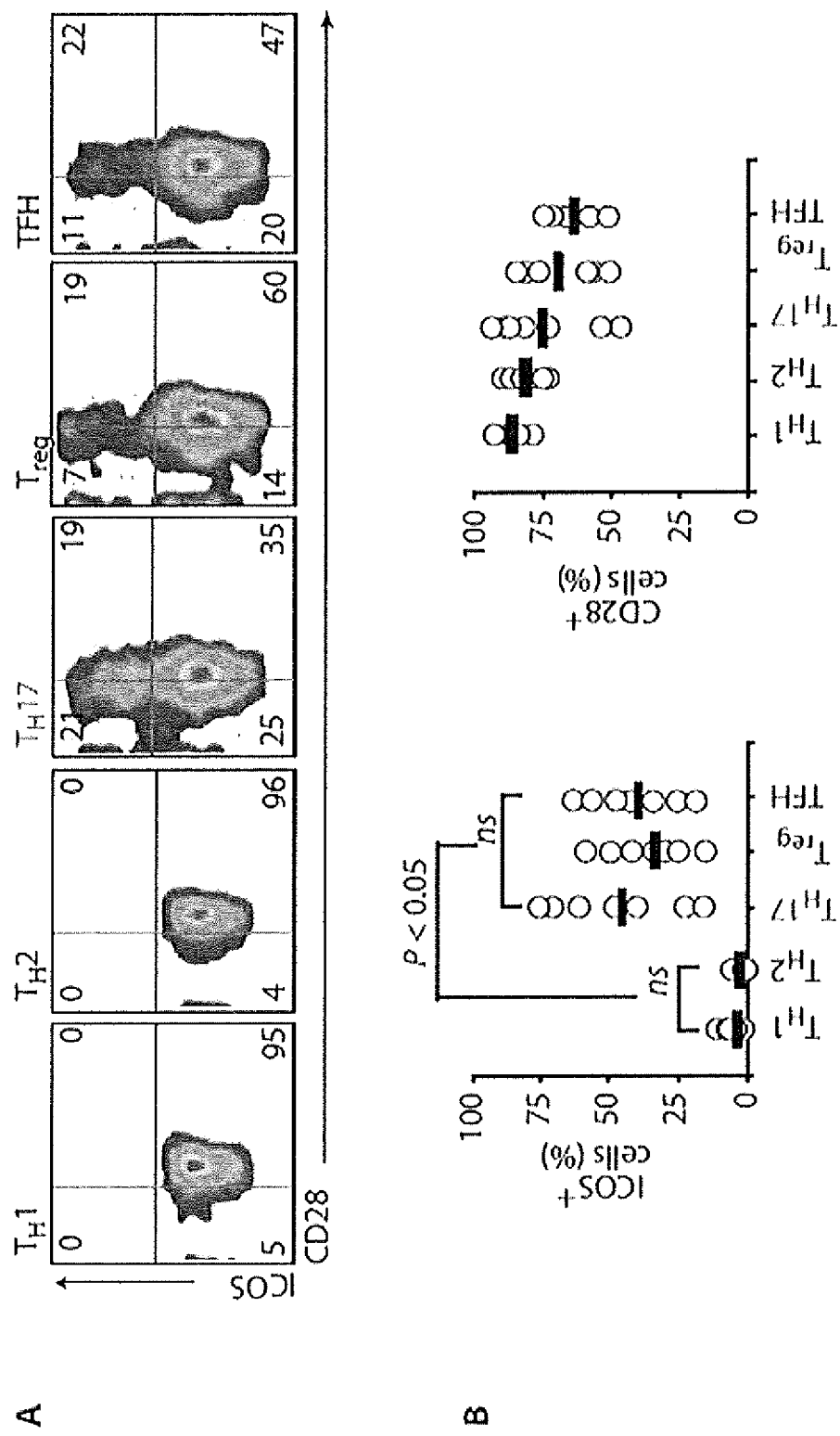
FIG. 1, comprising
Figure 1:
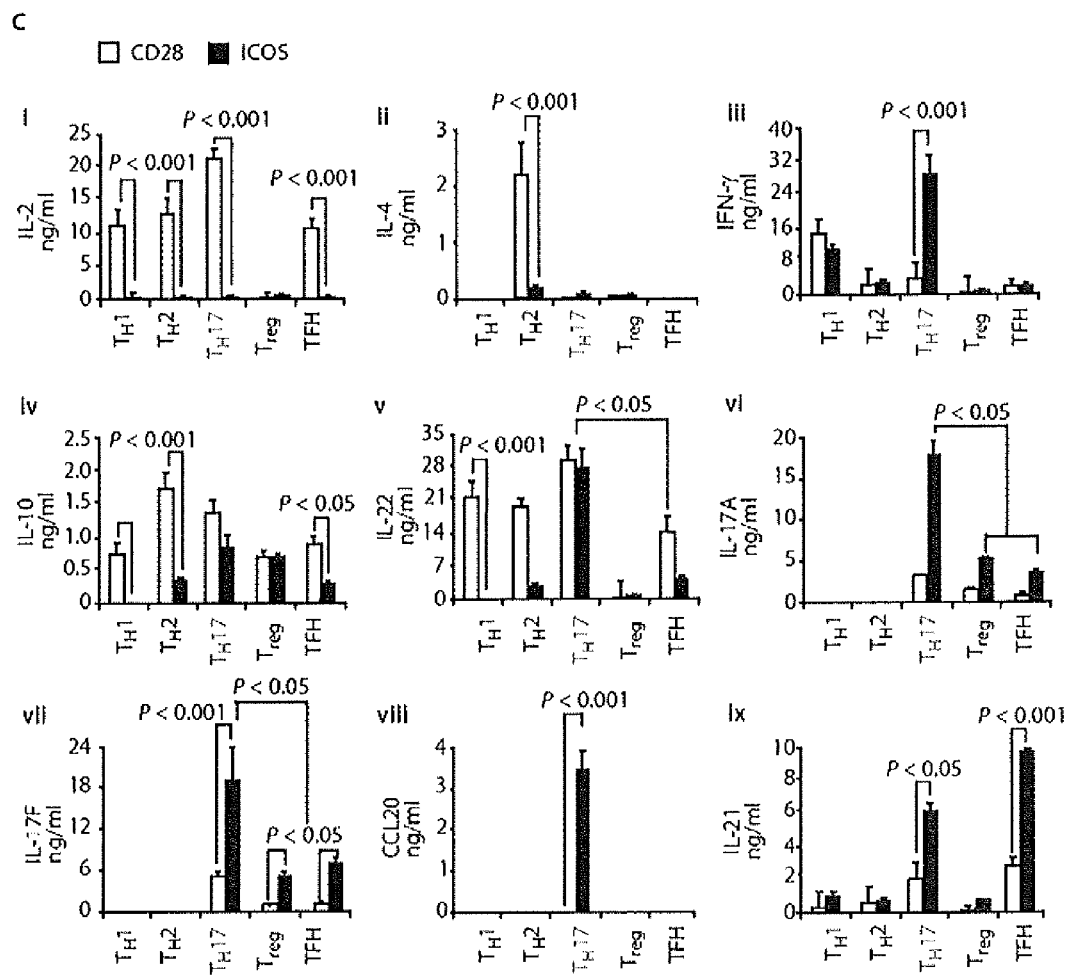

The present invention provides compositions and methods for their use to expand in vitro or in vivo a desired T cell, activate and/or expand specific T cell subsets, identify stimulatory molecules, co-stimulatory molecules, and combinations thereof, that can promote expansion of specific T cell subsets, as well as numerous therapeutic uses relating to expansion and stimulation of T cells. Preferably, the T cell is Th17.

The present invention is based on the discovery that human Th17 cell proliferation and function vary dramatically depending upon whether they receive CD28 or ICOS costimulation. The disclosure presented herein demonstrates that ICOS costimulation specifically promotes the outgrowth and augments the function of peripheral Th17 cells. In contrast, CD28 costimulation abrogates the effect of ICOS. The results presented herein demonstrate that costimulation of naive precursor cells from human cord blood with ICOS in the presence of Th17 polarizing agents support the generation and expansion of Th17 cells, as indicated by their capacity to secrete heightened levels of IL-17A, IL-17F and CCL20. ICOS costimulation not only can elevate Th17 cells to produce Th17-associated cytokines, but also elevate secretion of IFNγ, TNFα and IL-21 as compared with CD28 costimulation.

In one embodiment, ICOS costimulation on T cells can be accomplished by contacting the T cell with an artificial antigen presenting cell (aAPC) that comprises a molecule capable of activating ICOS on the T cell.

In another embodiment, the aAPC comprising a molecule capable of activating ICOS on T cells can further be engineered to comprise a cytokine that promotes Th17 differentiation. Such Th17 differentiation cytokines includes but are not limited to IL-2, IL-6, and IL-1.

In yet another embodiment, the aAPC comprising a molecule capable of activating ICOS on T cells can also be engineered to comprise an inhibitory molecule that can block a cytokine that interferes with the Th17 differentiation process. For example, the aAPC can be engineered to secrete a neutralizing antibody than can inhibit a cytokine that interferes with Th17 differentiation. A cytokine that interferes with Th17 differentiation process includes but is not limited to IFNγ and IL-4.

Of clinical importance, the Th17 cells generated according to the methods of the invention can be used in adoptive transfer immunotherapy. That is, human T cells expanded in the presence of ICOS costimulation mediate superior regression of established human tumors compared with an otherwise identical T cell expanded in the presence of CD28. In one embodiment, cells engineered to be able to activate ICOS on T cells can be used to boost and expand Th17 cells in vivo as a form of vaccination.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

An "amino acid" as used herein is meant to include both natural and synthetic amino acids, and both D and L amino acids. "Standard amino acid" means any of the twenty L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half life without adversely affecting activity of the peptide. Additionally, a disulfide linkage may be present or absent in the peptides.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "agent", "ligand", or "agent that binds a cell surface moiety", as used herein, refers to a molecule that binds to a defined population of cells. The agent may bind any cell surface moiety, such as a receptor, an antigenic determinant, or other binding site present on the target cell population. The agent may be a protein, peptide, antibody and antibody fragments thereof, fusion proteins, synthetic molecule, an organic molecule (e.g., a small molecule), a carbohydrate, or the like. Within the specification and in the context of T cell stimulation, antibodies and natural ligands are used as prototypical examples of such agents.

The terms "agent that binds a cell surface moiety" and "cell surface moiety", as used herein, are used in the context of a ligand/anti-ligand pair. Accordingly, these molecules should be viewed as a complementary/anti-complementary set of molecules that demonstrate specific binding, generally of relatively high affinity.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anti-codon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

As used herein, the term "fragment," as applied to a protein or peptide, refers to a subsequence of a larger protein or peptide. A "fragment" of a protein or peptide can be at least about 20 amino acids in length; for example at least about 50 amino acids in length; at least about 100 amino acids in length, at least about 200 amino acids in length, at least about 300 amino acids in length, and at least about 400 amino acids in length (and any integer value in between).

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. By way of example, the DNA sequences 5'-ATTGCC-3' and 5'-TATGGC-3' share 50% homology.

The term "immunoglobulin" or "Ig", as used herein is defined as a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most mammals. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the term "modulate" is meant to refer to any change in biological state, i.e. increasing, decreasing, and the like.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "T-helper" as used herein with reference to cells indicates a sub-group of lymphocytes (a type of white blood cell or leukocyte) including different cell types identifiable by a skilled person. In particular, T-helper cell according to the present disclosure include effector $T_h$ cells (such as Th1, Th2 and Th17). These Th cells secrete cytokines, proteins or peptides that stimulate or interact with other leukocytes.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

A "stimulatory molecule," as the term is used herein, means a molecule on a T cell that specifically binds with a cognate stimulatory ligand present on an antigen presenting cell (e.g., an aAPC of the invention, among others).

"Loaded" with a peptide, as used herein, refers to presentation of an antigen in the context of an MHC molecule. "Loaded" as used herein also means the binding of an antibody to an Fc binding receptor on a cell, such as CD32 and/or CD64.

A "co-stimulatory signal", as used herein, refers to a signal, which in combination with a primary signal, such as TCR/CD3 ligation, leads to T cell proliferation and/or upregulation or downregulation of key molecules.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

DESCRIPTION

The present invention is partly based on the observation that the nature of costimulation during CD4+ T cell activation critically regulates human Th17 cell differentiation. For example, ICOS, but not CD28, was found to be necessary for optimal expansion and function of human Th17 cells. Surprisingly, CD28 ligation abrogated the effects of ICOS costimulation. Of clinical relevance, genetically reprogrammed human Th17 cells expanded with ICOS mediated superior regression of human tumors compared to cells expanded with CD28. These findings reveal a key role for ICOS signaling in human Th17 cell development and suggest new therapeutic approaches.

The invention relates to the surprising discovery that ICOS costimulation of Th17 cells resulted in significantly higher levels of IL-17F, CCL20, and IL-21 production compared to the levels of IL-17F, CCL20, and IL-21 produced from an otherwise identical cell costimulated with CD28. In some instances, ICOS costimulation also resulted in elevated IL-17A secretion compared with the level of IL-17A secretion from an otherwise identical cell costimulated with CD28. In some instances, ICOS-stimulated Th17 cells also produced substantially greater amounts of IFNγ compared to CD28-stimulated Th1 cells, a subset previously thought to be a dominant source of IFNγ production.

Accordingly, the present invention includes compositions and methods for generating a population of human Th17 cells having unique inflammatory characteristics. For example, the ICOS-stimulated Th17 cells secrete high levels of IL-17 and CCL20 as well as produce elevated levels of IFNγ and IL-21 compared to CD28-stimulated Th1 cells. The present invention is based on the unexpected discovery that ICOS, but not CD28, costimulation preferentially expands Th17 cells. ICOS-costimulation provides a means to culture expand Th17 and maintain long-term culture of Th17 cells.

The present invention provides compositions and methods for their use to expand a Th17 cells as well as numerous therapeutic uses relating to expansion and stimulation of Th17 cells.

In one embodiment, the invention provides compositions and methods for generating therapeutic amounts of Th17 cells from peripheral or umbilical cord blood (UCB). In some instances, Th17 cells are generated from naïve precursor cells. Preferable, the naïve precursor cells are CD45RA+CD25− cells.

Composition

The invention pertains to compositions comprising an agent that provides a costimulatory signal to a T cell for T cell expansion (e.g., ICOSL). In some instances, the costimulatory signal is provided to a T cell in combination with an agent that provides a primary activation signal to the T cell (e.g., a TCR/CD3 complex). For example, an agent that provides a primary activation signal to the T cell is an anti-CD3 antibody.

In some instances, the agent (primary, costimulatory, or combination thereof) is preferably attached to beads. Compositions of the invention can also include those comprising more than one type of agent coupled to different solid phase surfaces (i.e., an agent that provides a primary T cell activation signal coupled to a first solid phase surface and an agent that provides a costimulatory signal coupled to a second solid phase surface).

Alternatively, the agent (primary, costimulatory, or combination thereof) is in the context of being displayed on an artificial antigen presenting cell (aAPC). Accordingly, the invention includes any means of promoting ICOS engagement of T cells using either a solid phase surface (e.g., beads) or a cell (e.g., aAPC). That is, there is extensive knowledge in the art regarding the events and molecules involved in activation and induction of T cell. However, the invention is based on the unexpected discovery that ICOS engagement, but not CD28 costimulation, preferentially expands cells having a Th17 phenotype.

The extensive disclosure provided in WO 03/057171 and US2003/0147869 is incorporated by reference as if set forth in its entirety herein. More specifically, a primary signal, usually mediated via the T cell receptor/CD3 complex on a T cell, initiates the T cell activation process. Additionally, numerous co-stimulatory molecules present on the surface of a T cell are involved in regulating the transition from resting T cell to cell proliferation. Such co-stimulatory molecules, also referred to as "co-stimulators", which specifically bind with their respective ligands, include, but are not limited to, CD28 (which binds with B7-1 [CD80], B7-2 [CD86]), PD-1 (which binds with ligands PD-L1 and PD-L2), B7-H3, 4-1BB (binds the ligand 4-1BBL), OX40 (binds ligand OX40L), ICOS (binds ligand ICOS-L), and LFA (binds the ligand ICAM). Thus, the primary stimulatory signal mediates T cell stimulation, but the co-stimulatory signal is then required for T cell activation, as demonstrated by proliferation.

T cell activation can be accomplished by stimulating the T cell TCR/CD3 complex or via stimulation of the CD2 surface protein. An anti-CD3 monoclonal antibody can be used to activate a population of T cells via the TCR/CD3 complex. Although a number of anti-human CD3 monoclonal antibodies are commercially available, OKT3 prepared from hybridoma cells obtained from the American Type Culture Collection or monoclonal antibody G19-4 is preferred. Similarly, binding of an anti-CD2 antibody will activate T cells. Stimulatory forms of anti-CD2 antibodies are known and available.

A primary activation signal can also be delivered to a T cell through use of a combination of a protein kinase C (PKC) activator such as a phorbol ester (e.g., phorbol myristate acetate) and a calcium ionophore (e.g., ionomycin which raises cytoplasmic calcium concentrations). The use of these agents bypasses the TCR/CD3 complex but delivers a stimulatory signal to T cells. These agents are also known to exert a synergistic effect on T cells to promote T cell activation and can be used in the absence of antigen to deliver a primary activation signal to T cells.

Although stimulation of the TCR/CD3 complex or CD2 molecule is required for delivery of a primary activation signal in a T cell, a number of molecules on the surface of T cells, termed accessory or costimulatory molecules have been implicated in regulating the transition of a resting T cell to blast transformation, and subsequent proliferation and differentiation. Thus, in addition to the primary activation signal provided through the TCR/CD3 complex, induction of T cell responses requires a second, costimulatory signal. One such costimulatory or accessory molecule, CD28, is believed to initiate or regulate a signal transduction pathway that is distinct from those stimulated by the TCR complex. However, the invention is based on the discovery that ICOS, but not CD28 costimulation, preferentially expands cells having a Th17 phenotype. Moreover, combined CD28 and ICOS costimulation does not potentiate, but rather specifically reduces Th17 phenotype. This discovery was surprising because of the extensive use of CD28 in the art to expand Th17.

Accordingly, the invention relates to the use of compositions that can promote ICOS costimulation on T cells. Any agent that can induce stimulation of the ICOS molecule is encompassed by the invention. In addition, binding homologues of a natural ligand, whether native or synthesized by chemical or recombinant technique, can also be used in accordance with the invention. Ligands useful for stimulating an ICOS can be used in soluble form, attached to the surface of a cell, or immobilized on a solid phase surface as described herein. Anti-ICOS antibodies or fragments thereof are also useful in stimulating ICOS molecule.

In a specific embodiment of the invention, activated T cells are contacted with a stimulatory form of a natural ligand for ICOS for costimulation. The natural ligand of ICOS is referred in the art as ICOSL. A "stimulatory form of a natural ligand for ICOS" is a form of a natural ligand that is able to bind to ICOS and costimulate the T cell. Costimulation can be evidenced by proliferation and/or cytokine production by T cells that have received a primary activation signal, such as stimulation through the CD3/TCR complex or through CD2.

In a preferred embodiment of the invention, an ICOSL molecule is localized on the surface of a cell. This can be accomplished by transfecting a cell with a nucleic acid encoding the ICOSL molecule in a form suitable for its expression on the cell surface or alternatively by coupling a ICOSL molecule to the cell surface. Alternatively, an anti-ICOS antibody can be "loaded" to the cell surface of an aAPC. That is, the skilled artisan would understand, based upon the disclosure provided herein, that an aAPC comprising an antibody can be produced, as exemplified elsewhere herein, by introducing a nucleic acid encoding a human Fcγ receptor (e.g., CD32 or CD64), into the aAPC. The CD32 and/or CD64 expressed on the aAPC surface can then be "loaded" with any desired antibody that binds with CD32 and/or CD64, including, but not limited to, antibody that specifically binds CD3 and antibody that specifically binds with ICOS.

One of ordinary skill in the art will recognize that any agent, including an anti-ICOS antibody or fragment thereof capable of cross-linking the ICOS molecule, or a natural ligand for ICOS can be used to stimulate T cells. In particular, human ICOS ligand can be cloned from the appropriate cell into the pcDNA3 or other suitable vectors and be transfected into an aAPC.

Moreover, the invention encompasses an aAPC wherein a nucleic acid encoding the antibody ligand of interest, optionally linked to an IRES sequence, is transduced and expressed on the surface of the aAPC thereby eliminating the need for expression of CD32 and/or CD64 and loading thereof. Thus, the present invention includes an aAPC transduced with a nucleic acid encoding at least one antibody that specifically binds with a molecule associated with a primary activation signal and ICOS, among others, as well as an aAPC transduced with CD32 and/or CD64 and loaded with at least one antibody that specifically binds with the afore-mentioned molecules.

Soluble Forms of ICOSL as Costimulator

The natural ligands of ICOS can also be presented to T cells in soluble form. Soluble forms of ICOSL molecules include natural ICOSL molecules, a fragment thereof, or modified form of the full length or fragment of the ICOSL molecule that is able to bind to ICOS and costimulate the T cell. Costimulation can be evidenced by proliferation and/or cyotkine production by T cells that have received a primary activation signal. Modifications of ICOSL molecules include modifications that preferably enhance the affinity of binding of ICOSL molecules to ICOS molecules, but also modifications that diminish or do not affect the affinity of binding of ICOSL molecules to ICOS molecules. Modifications of ICOSL molecules also include those that increase the stability of a soluble form of a ICOSL molecule. The modifications of ICOS molecules are usually produced by amino acid substitutions, but can also be produced by linkage to another molecule.

In one specific embodiment, the soluble form of an ICOSL molecule is a fusion protein containing a first peptide consisting of an ICOSL molecule, or fragment thereof and a second peptide corresponding to a moiety that alters the solubility, binding, affinity, stability, or valency (i.e., the number of binding sites available per molecule) of the first peptide. Preferably, the first peptide includes an extracellular domain portion of an ICOSL molecule that interacts with ICOS and is able to provide a costimulatory signal as evidenced by stimulation of proliferation of T cells or secretion of cytokines from the T cells upon exposure to the ICOSL fusion protein and a primary T cell activation signal.

Fusion proteins within the scope of the invention can be prepared by expression of a nucleic acid encoding the fusion protein in a variety of different systems. Typically, the nucleic acid encoding an ICOSL fusion protein comprises a first nucleotide sequence encoding a first peptide consisting of an ICOSL molecule or a fragment thereof and a second nucleotide sequence encoding a second peptide corresponding to a moiety that alters the solubility, binding, stability, or valency of the first peptide, such as an immunoglobulin constant region. Nucleic acid encoding a peptide comprising an immunoglobulin constant region can be obtained from human immunoglobulin mRNA present in B lymphocytes. It is also possible to obtain nucleic acid encoding an immunoglobulin constant region from B cell genomic DNA. For example, DNA encoding Cγ1 or Cγ4 can be cloned from either a cDNA or a genomic library or by polymerase chain reaction (PCR) amplification in accordance standard protocols. A preferred nucleic acid encoding an immunoglobulin constant region comprises all or a portion of the following: the DNA encoding human Cγ1 (Takahashi, N. S. et al. (1982) Cell 29:671-679), the DNA encoding human Cγ2; the DNA encoding human Cγ3 (Huck, S., et al. (1986) Nucl. Acid Res. 14:1779); and the DNA encoding human Cγ4. When an immunoglobulin constant region is used in the ICOSL fusion protein, the constant region can be modified to reduce at least one constant region mediated biological effector function. For example, DNA encoding a Cγ1 or Cγ4 constant region can be modified by PCR mutagenesis or site directed mutagenesis. Protocols and reagents for site directed mutagenesis systems can be obtained commercially from Amersham International PLC, Amersham, UK.

In one embodiment the first and second nucleotide sequences are linked (i.e., in a 5' to 3' orientation by phosphodiester bonds) such that the translational frame of the ICOSL protein or fragment thereof and the IgC (i.e., Fc fragment that comprises the hinge, CH2, and CH3 regions of human IgG) coding segments are maintained (i.e., the nucleotide sequences are joined together in-frame). Thus, expression (i.e., transcription and translation) of the nucleotide sequence produces a functional ICOSLIg fusion protein. The nucleic acids of the invention can be prepared by standard recombinant DNA techniques. For example, an ICOSLIg fusion protein can be constructed using separate template DNAs encoding ICOSL and an immunoglobulin constant region. The appropriate segments of each template DNA can be amplified by polymerase chain reaction (PCR) and ligated in frame using standard techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

The following is a description of molecular biology techniques applicable for generating soluble ICOSL. However, these molecular biology techniques can be applied to generate ICOSL presented in the context of any form encompassed by the present invention (e.g., displayed on a solid phase support, aAPC, and the like).

The nucleic acids encoding ICOSL molecules or ICLOSLIg fusion proteins can be inserted into various expression vectors, which in turn direct the synthesis of the corresponding protein in a variety of hosts, particularly eucaryotic cells, such as mammalian or insect cell culture and procaryotic cells, such as E. coli. Expression vectors within the scope of the invention comprise a nucleic acid as described herein and a promoter operably linked to the nucleic acid. Such expression vectors can be used to transfect host cells to thereby produce fusion proteins encoded by nucleic acids as described herein. An expression vector of the invention, as described herein, typically includes nucleotide sequences encoding an ICOSL molecule or ICOSLIg fusion protein operably linked to at least one regulatory sequence.

An expression vector of the invention can be used to transfect cells, either procaryotic or eucaryotic (e.g., mammalian, insect or yeast cells) to thereby produce fusion proteins encoded by nucleotide sequences of the vector. Expression in procaryotes is most often carried out in E. coli with vectors containing constitutive or inducible promoters. Certain E. coli expression vectors (so called fusion-vectors) are designed to add a number of amino acid residues to the expressed recombinant protein, usually to the amino terminus of the expressed protein. Such fusion vectors typically serve three purposes: 1) to increase expression of recombinant protein; 2) to increase the solubility of the target recombinant protein; and 3) to aid in the purification of the target recombinant protein by acting as a ligand in affinity purification. Examples of fusion expression vectors include pGEX (Amrad Corp., Melbourne, Australia) and pMAL (New England Biolabs, Beverly, Mass.) which fuse glutathione S-tranferase and maltose E binding protein, respectively, to the target recombinant protein. Accordingly, an ICOSL molecule or ICOSLIg fusion gene may be linked to additional coding sequences in a procaryotic fusion vector to aid in the expression, solubility or purification of the fusion protein. Often, in fusion expression vectors, a proteolytic cleavage site is introduced at the junction of the fusion moiety and the target recombinant protein to enable separation of the target recombinant protein from the fusion moiety subsequent to purification of the fusion protein. Such enzymes, and their cognate recognition sequences, include Factor Xa, thrombin and enterokinase.

One strategy to maximize expression of an ICOSL molecule or ICOSLIg fusion protein in E. coli is to express the protein in a host bacterium with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleotide sequence of the ICOSL molecule or ICOSLIg fusion protein construct to be inserted into an expression vector so that the individual codons for each amino acid would be those preferentially utilized in highly expressed E. coli proteins (Wada et al., (1992) Nuc. Acids Res. 20:2111-2118). Such alteration of nucleic acid sequences are encompassed by the invention and can be carried out using standard DNA synthesis techniques.

Alternatively, an ICOSL molecule or ICOSLIg fusion protein can be expressed in a eucaryotic host cell, such as mammalian cells (e.g., Chinese hamster ovary cells (CHO) or NS0 cells), insect cells (e.g., using a baculovirus vector) or yeast cells. Other suitable host cells are known to those skilled in the art. Eucaryotic, rather than procaryotic, expression of an ICOSL molecule or ICOSLIg fusion protein may be preferable since expression of eucaryotic proteins in eucaryotic cells can lead to partial or complete glycosylation and/or formation of relevant inter- or intra-chain disulfide bonds of a recombinant protein. For expression in mammalian cells, the expression vector's control functions are often provided by viral material.

Vector DNA can be introduced into procaryotic or eucaryotic cells via conventional transformation or transfection techniques such as calcium phosphate or calcium chloride co-precipitation, DEAE-dextran-mediated transfection, lipofection, or electroporation. Suitable methods for transforming host cells can be found in Sambrook et al (Molecular Cloning: A Laboratory Manual, 2nd Edition, Cold Spring Harbor Laboratory press (2001)), and other laboratory textbooks.

For stable transfection of mammalian cells, it is known that, depending upon the expression vector and transfection technique used, only a small faction of cells may integrate DNA into their genomes. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same plasmid as the gene of interest or may be introduced on a separate plasmid. Cells containing the gene of interest can be identified by drug selection (e.g., cells that have incorporated the selectable marker gene will survive, while the other cells die). The surviving cells can then be screened for production of ICOSL molecules or ICOSLIg fusion proteins by, for example, immunoprecipitation from cell supernatant with an anti-ICOSL monoclonal antibody.

ICOSL molecule or ICOSLIg fusion proteins produced by recombinant technique may be secreted and isolated from a mixture of cells and medium containing the protein. Alternatively, the protein may be retained cytoplasmically and the cells harvested, lysed and the protein isolated. A cell culture typically includes host cells, media and other byproducts.

Suitable mediums for cell culture are well known in the art. Protein can be isolated from cell culture medium, host cells, or both using techniques known in the art for purifying proteins.

For T cell costimulation, the soluble form of the natural ligand for ICOSL is added to the T cell culture in an amount sufficient to result in costimulation of activated T cells. The appropriate amount of soluble ligand to be added will vary with the specific ligand, but can be determined by assaying different amounts of the soluble ligand in T cell cultures and measuring the extent of costimulation by proliferation assays or production of cytokines, as described in the Examples.

Coupling of the Natural Ligands to a Solid Phase Surface

In another embodiment of the invention, a natural ligand of ICOS can be presented to T cells in a form attached to a solid phase surface, such as beads. The ICOSL molecules, fragments thereof or modified forms thereof capable of binding to ICOS and costimulating the T cells can be prepared as described for the soluble ICOSL forms. These molecules can then be attached to the solid phase surface via several methods. For example the ICOSL molecules can be crosslinked to the beads via covalent modification using tosyl linkage. In this method, ICOSL molecules or ICOSL fusion proteins are in 0.05M borate buffer, pH 9.5 and added to tosyl activated magnetic immunobeads (Dynal Inc., Great Neck, N.Y.) according to manufacturer's instructions. After a 24 hr incubation at 22° C., the beads are collected and washed extensively. It is not mandatory that immunomagnetic beads be used, as other methods are also satisfactory. For example, the ICOSL molecules may also be immobilized on polystyrene beads or culture vessel surfaces. Covalent binding of the ICOSL molecules or ICOSLIg fusion proteins to the solid phase surface is preferable to adsorption or capture by a secondary monoclonal antibody. ICOSLIg fusion proteins can be attached to the solid phase surface through anti-human IgG molecules bound to the solid phase surface. These beads can then be incubated with the ICOSLIg fusion proteins in an appropriate buffer such as PBS for about an hour at 5° C., and the uncoupled ICOSLIg proteins removed by washing the beads in a buffer, such as PBS.

It is also possible to attach the ICOSL molecules to the solid phase surface through an avidin- or streptavidin-biotin complex. In this particular embodiment, the soluble ICOSL molecule is first crosslinked to biotin and then reacted with the solid phase surface to which avidin or streptavidin molecules are bound. It is also possible to crosslink the ICOSL molecules with avidin or streptavidin and to react these with a solid phase surface that is covered with biotin molecules.

The amount of ICOSL molecules attached to the solid phase surface can be determined by FACS analysis if the solid phase surface is that of beads or by ELISA if the solid phase surface is that of a tissue culture dish. Antibodies reactive with the ICOSL molecules can be used in these assays.

In a specific embodiment, the stimulatory form of an ICOSL molecule is attached to the same solid phase surface as the agent that stimulates the TCR/CD3 complex, such as an anti-CD3 antibody. In addition to anti-CD3, other antibodies that bind to receptors that mimic antigen signals may be used, for example, the beads or other solid phase surface may be coated with combinations of anti-CD2 and an ICOSL molecule.

In a typical experiment, ICOSL-coated beads or beads coated with ICOSL molecules and an agent that stimulates the TCR/CD3 complex will be added at a ratio of 3 beads per T cell. However, the ratio can be adjusted to provide a desirable result.

Artificial Antigen Presenting Cell (aAPC)

The invention encompasses an aAPC wherein the co-stimulatory ligand is a cognate binding partner that specifically binds with a co-stimulatory molecule, as well as where the ligand is an antibody that specifically binds with a costimulatory molecule, and any combination thereof, such that a single aAPC can comprise both nucleic acids encoding costimulatory ligands and/or antibodies specific for costimulatory molecules present on the T cell, and any combination thereof. The extensive disclosure regarding aAPCs provided in WO 03/057171 and US2003/0147869 is incorporated by reference as if set forth in its entirety herein. However, the present invention is based on the surprising discovery that ICOS costimulation rather than CD28 costimulation preferentially expands cells with a Th17 phenotype.

The invention also encompasses an aAPC comprising a nucleic acid encoding an antigen of interest. A wide plethora of antigens are included, such as, but not limited to, tumor antigens, e.g., telomerase, melanoma antigen recognized by T cells (MART-1), melanoma antigen-encoding genes, 1, 2, and 3 (MAGE-1, -2, -3), melanoma GP100, carcinoembryonic antigen (CEA), breast cancer antigen HER-2/Neu, serum prostate specific antigen (PSA), Wilm's Tumor 1 (WT-1), mucin antigens (MUC-1, -2, -3, -4), and B cell lymphoma idiotypes. This is because, as demonstrated by the data disclosed elsewhere herein, K562-based aAPC comprising an antigen, can process and present the antigen in the context of MHC (where the cell is also transduced with a nucleic acid encoding a MHC class I or class II molecule) thereby producing antigen-specific T cells and expanding a population thereof. The data disclosed demonstrate that T-cells expanded with anti-CD3/ICOS beads or anti-CD3/ICOSL expressing aAPC, and then genetically modified with a chimeric immunoreceptor to confer specificity for mesothelin-expressing tumors exhibited antitumor activity. Thus, aAPCs can be used to expand and produce sufficient antigen specific T cells in order to administer the T cells to a patient in need thereof thus providing an immunovaccine treatment directed against tumor cells bearing the antigen. Alternatively, the aAPCs can be administered directly to the patient as another form of immunovaccination. Therefore, an antigen of interest can be introduced into an aAPC of the invention, wherein the aAPC then presents the antigen in the context of the MCH Class I or II complex, i.e., the MHC molecule is "loaded" with the antigen, and the aAPC can be used to produce an antigen-specific T cell. Alternatively, the aAPC can be used to expand the T cells in vitro or in vivo. and the expanded T cell can be further modified to become antigen specific.

In one embodiment, the invention includes a T cell that has been expanded with at least by ICOS costimulation and the expanded T cell is further modified to render the ICOS costimulated T cell antigen specific. For example, an ICOS costimulated T cell may become Ag-specific in vitro, e.g., genetically modified with the ICOS costimulated T cell to confer specificity for a desired antigen. The ICOS costimulated T cell may be transfected with a vector which allows for the expression of a specific antigen by the ICOS costimulated T cell.

In another embodiment, the invention uses ICOSL aAPC to boost T cells in vivo. The T cells may have previously been engineered in vitro and after infusion to a patient, boosted with the ICOSL aAPC vaccination. Alternatively, the ICOSL aAPC may be loaded with antigens and used as a priming vaccine to stimulate a Th17 response.

As discussed elsewhere herein, vectors may be prepared to include a specific polynucleotide which encodes and expresses a protein to which an immunogenic response is desired. As discussed elsewhere herein, various methods can be used for transfecting a polynucleotide into a host cell. The methods include, but are not limited to, calcium phosphate precipitation, lipofection, particle bombardment, microinjection, electroporation, colloidal dispersion systems (i.e. macromolecule complexes, nanocapsules, microspheres, beads, and lipid-based systems including oil-in-water emulsions, micelles, mixed micelles, and liposomes).

A polynucleotide encoding an antigen can be cloned into an expression vector and the vector can be introduced into an ICOS costimulated T cell to otherwise generate an ICOS costimulated antigen specific T cell. Various types of vectors and methods of introducing nucleic acids into a cell are discussed elsewhere herein. For example, a vector encoding an antigen may be introduced into a host cell by any method in the art. For example, the expression vector can be transferred into a host cell by physical, chemical or biological means. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The antigen of interest may be derived from a virus, a fungus, or a bacterium. The antigen may be a self-antigen or an antigen associated with a disease selected from the group consisting of an infectious disease, a cancer, an autoimmune disease.

In certain embodiments, an immune response may be promoted by introducing the ICOS costimulated antigen specific T cell into a mammal. For an antigenic composition to be useful as a vaccine, the antigenic composition must induce an immune response to the antigen in a cell, tissue or mammal (e.g., a human). As used herein, an "immunological composition" may comprise an antigen (e.g., a peptide or polypeptide), a nucleic acid encoding an antigen (e.g., an antigen expression vector), a cell expressing or presenting an antigen or cellular component. In particular embodiments the antigenic composition comprises or encodes all or part of any antigen described herein, or an immunologically functional equivalent thereof.

In the context of the present invention, "tumor antigen" or "hyperproliferative disorder antigen" or "antigen associated with a hyperproliferative disorder" refer to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

In one embodiment, the tumor antigen of the present invention comprises one or more antigenic cancer epitopes immunologically recognized by tumor infiltrating lymphocytes (TIL) derived from a cancer tumor of a mammal.

Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD 19, CD20, idiotype) have been used as targets for passive immunotherapy with monoclonal antibodies with limited success.

The tumor antigen and the antigenic cancer epitopes thereof may be purified and isolated from natural sources such as from primary clinical isolates, cell lines and the like. The cancer peptides and their antigenic epitopes may also be obtained by chemical synthesis or by recombinant DNA techniques known in the arts. Techniques for chemical synthesis are described in Steward et al. (1969); Bodansky et al. (1976); Meienhofer (1983); and Schroder et al. (1965). Furthermore, as described in Renkvist et al. (2001), there are numerous antigens known in the art. The following tables describe T cell-defined epitopes encoded by tumor antigens, and only those tumor antigens recognized by T cells (either cytotoxic CD8+ or helper CD4+) are listed. Although analogs or artificially modified epitopes are not listed, a skilled artisan recognizes how to obtain or generate them by standard means in the art. Other antigens, identified by antibodies and as detected by the Serex technology (see Sahin et al. (1997) and Chen et al. (2000)), are identified in the database of the Ludwig Institute for Cancer Research.

Sources of T Cells

Prior to expansion, a source of T cells is obtained from a subject. Examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations.

T cells for stimulation can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

Stimulation of a Cell Population

As noted herein, the present invention provides compositions and methods for stimulating a cell population by binding moieties on the surfaces of the cells in that population. Contacting a cell population with an agent (e.g., a ligand) that binds to a cell surface moiety can stimulate the cell population. The ligand may be in solution but also may be attached to a surface. Ligation of cell surface moieties, such as a receptor, may generally induce a particular signaling pathway.

The methods of the present invention relate to the stimulation of a target cell by introducing a ligand or agent that binds to a cellular moiety, thereby inducing a cellular event. Binding of the ligand or agent to the cell may trigger a signaling pathway that in turn activates particular phenotypic or biological changes in the cell. The stimulation of a target cell by introducing a ligand or agent that binds to a cellular moiety as described herein may upregulate or downregulate any number of cellular processes leading to particular phenotypic or biological changes in the cell. The activation of the cell may enhance normal cellular functions or initiate normal cell functions in an abnormal cell. The method described herein provides stimulation by contacting the cells with the ligand or agent that binds a cell surface moiety. Stimulation of a cell may be enhanced or a particular cellular event may be stimulated by introducing a second agent or ligand that ligates a second cell surface moiety. This method may be applied to any cell for which ligation of a cell surface moiety leads to a signaling event. The invention further provides means for selection or culturing the stimulated cells.

In one embodiment, umbilical cord blood cells are stimulated according to the present invention related to ICOS costimulation. For example, umbilical cord blood cells can be stimulated with either anti-CD3/anti-ICOS beads or with ICOSL-expressing aAPCs, in the presence of Th17-polarizing cytokines. An example of Th17-polarizing cytokines include but is not limited to IL-6, IL-1β and IL-23 cytokines and neutralizing IFNγ and IL-4 antibodies. Accordingly, the present invention provides a means to expand Th17 precursor cells. This aspect of the invention is based on the unexpected finding that ICOS costimulation of CD4+ T cells in the presence of Th17-polarizing cytokines resulted in elevated secretion of IL-17A, while virtually none of the cells engaged with CD28 produced IL-17A.

In one particular embodiment of the invention, a T cell may be stimulated by contacting an agent with a cell surface moiety on the T cell. In one aspect of the present invention, antibodies to CD3 and ICOS are loaded onto an aAPC. In another aspect of the present invention, any ligand that binds the TCR/CD3 complex and initiates a primary stimulation signal may be utilized as a primary activation agent loaded onto or expressed by the aAPC. Any ligand that binds ICOS and initiates the ICOS signal transduction pathway, thus causing co-stimulation of the cell with a CD3 ligand and enhancing activation of a population of T cells, is an ICOS ligand and accordingly, is a co-stimulatory agent within the context of the present invention.

In other aspects of the present invention, T cells can be exposed to a bead comprising a first agent that binds the TCR/CD3 complex and initiates a primary stimulation signal and a second agent that binds ICOS and initiates the ICOS signal transduction pathway, thus causing co-stimulation of the cell with a CD3 ligand and enhancing activation of a population of T cells.

Cells stimulated by the methods of the present invention are activated as shown by the induction of signal transduction, expression of cell surface markers and/or proliferation. Markers appropriate for Th17 cells include but are not limited to their capacity to secrete heightened levels of IL-17A, IL-17F and CCL20. Moreover, cells generated and expanded according to the ICOS costimulation method of the invention not only exhibit elevated production of Th17-associated cytokines but also exhibit elevated secretion of IFNγ, TNFα and IL-21 compared to CD28 costimulated cells.

In the context of generating Th17 cells by way of stimulating ICOS on T cells, an aAPC can be engineered to comprise a first agent that binds to TCR/CD3 complex of the T cell and a second agent that binds ICOS, the aAPC can further be engineered to comprise a cytokine that promotes Th17 differentiation. Exemplary Th17 differentiating cytokines include but are not limited to IL-2, IL-6, IL-23, and IL-1.

Accordingly, in certain aspects, the present invention includes aAPC that have been genetically modified to express stimulatory agents, co-stimulatory agents, and/or cytokines as well as other polypeptides. The invention encompasses an aAPC transduced with a nucleic acid encoding at least one cytokine. The aAPC can be engineered to express and secrete any desirable cytokine the promotes Th17 differentiation using the methods disclosed herein or known methods in the art for genetically modifying a cell.

Thus, the invention encompasses a cytokine, including a full-length, fragment, homologue, variant or mutant of the cytokine. A cytokine includes a protein that is capable of affecting the biological function of another cell. A biological function affected by a cytokine can include, but is not limited to, cell growth, cell differentiation or cell death. Preferably, a cytokine of the present invention is capable of binding to a specific receptor on the surface of a cell, thereby affecting the biological function of a cell. Preferably, the cytokine promotes Th17 differentiation.

A preferred cytokine includes, among others, a hematopoietic growth factor, an interleukin, an interferon, an immunoglobulin superfamily molecule, a tumor necrosis factor family molecule and/or a chemokine. A cytokine of the invention includes but is not limited to granulocyte macrophage colony stimulating factor (GM-CSF), tumor necrosis factor alpha (TNFα), tumor necrosis factor beta (TNFβ), macrophage colony stimulating factor (M-CSF), interleukin-1 (IL-1), interleukin-2 (IL-2), interleukin-4 (IL-4), interleukin-5 (IL-5), interleukin-6 (IL-6), interleukin-10 (IL-10), interleukin-12 (IL-12), interleukin-15 (IL-15), interleukin-21 (IL-21), interleukin-23 (IL-23), interferon alpha (IFNα), interferon beta (IFNβ), interferon gamma (IFNγ), and IGIF, among many others. A more preferred cytokine of the invention includes a cytokine that promotes Th17 differentiation including but not limited to IL-2, IL-6, IL-1 (e.g., IL-β). One skilled in the art would appreciate, once armed with the teachings provided herein, that the invention encompasses any Th17 differentiation promoting cytokine, such as those known in the art, as well as any discovered in the future.

In addition to engineering an aAPC to comprise a Th17 differentiation promoting cytokine, the aAPC can be engineered to comprise an inhibitory molecule that can block a cytokine that interferes with the Th17 differentiation process. For example, the aAPC can be engineered to secrete a neutralizing antibody than can inhibit a cytokine that interferes with Th17 differentiation. A cytokine that interferes with Th17 differentiation process includes but is not limited to IFNγ and IL-4.

When the aAPC has been engineered to express a desired cytokine that promotes Th17 differentiation and/or inhibitor of a cytokine that interferes with Th17 differentiation, the invention provides a method for activating and/or stimulating a population of T cells to promote Th17 differentiation in the absence of exogenously added cytokines. Further, such Th17 differentiation may occur in vivo.

In another embodiment, ICOS stimulated cells of the invention can be further manipulated to be antigen specific. For example, ICOS stimulated cells can be further genetically redirected to exhibit antitumor activity. In one embodiment, T cells are subjected to ICOS costimulation in the presence of Th17 polarizing cytokines (IL-1β, IL-6, IL-23, and neutralizing antibodies against IL-4 and IFNγ). These ICOS stimulated cells, upon genetic redirection, can mediate superior tumor regression compared with cells traditionally expanded with CD28. For example, T cells are expanded with anti-CD3/ICOSL, and then genetically modified with a chimeric immunoreceptor to confer specificity for a desired tumor antigen. This aspect of the invention is based on the discovery that, under Th17 polarizing conditions, ICOS signaling promotes the generation of inflammatory human T cells with an antitumor capacity exceeding those generated with CD28. The benefits of ICOS signaling over CD28 was an unexpected discovery because prior to the present invention, the CD28 costimulatory molecule was considered the preferred used to expand human T cells.

Those of ordinary skill in the art will readily appreciate that the cell stimulation methodologies described herein may be carried out in a variety of environments (i.e., containers). For example, such containers may be culture flasks, culture bags, or any container capable of holding cells, preferably in a sterile environment. In one embodiment of the present invention a bioreactor is also useful. For example, several manufacturers currently make devices that can be used to grow cells and be used in combination with the methods of the present invention. See for example, patents covering bioreactors such as U.S. Pat. Nos. 6,096,532; 5,985,653; 5,888,807; 5,190,878, each of which is incorporated herein by reference in their entirety.

Cell Populations

T helper cells (also known as effector T cells or Th cells) are a sub-group of lymphocytes (a type of white blood cell or leukocyte) that plays an important role in establishing and maximizing the capabilities of the immune system and in particular in activating and directing other immune cells. Different types of Th cells have been identified that originate in outcome of a differentiation process and are associated with a specific phenotype. Following T cell development, matured, naive (meaning they have never been exposed to the antigen to which they can respond) T cells leave the thymus and begin to spread throughout the body. Naive T cells can differentiate into a T-helper 1 (Th1), T-helper 2 (Th2), T-helper 17 (Th17) or regulatory T cell (Treg) phenotype.

Each of these Th cell types secretes cytokines, proteins or peptides that stimulate or interact with other leukocytes, including Th cells. However, each cell type has a peculiar phenotype and activity that interferes and often conflict with the other.

Th1, Th2, and Th17 (inflammatory T-helper or inflammatory Th), promote inflammation responses trough secretion of pro-inflammatory cytokines, such as IL-1, IL-6, TNF-α, IL-17, IL21, IL23, and/or through activation and/or inhibition of other T cell including other Th cells (for example Th1 cell suppresses Th2 and Th17, Th2 suppresses Th1 and Th17). Tregs instead, are a component of the immune system that suppresses biological activities of other cells associated to an immune response. In particular, Tregs can secrete immunosuppressive cytokines TGF-β and Interleukin 10, and are known to be able to limit or suppress inflammation.

The present invention is based on the discovery that ICOS costimulation attributes to expansion of Th17 cells. For example, CD4+ T cells were activated in the presence of Th17-polarizing cytokines with ICOS costimulation exhibited characteristics of Th17. Such methodologies can be used therapeutically in an ex vivo setting to activate and stimulate cells for infusion into a patient or could be used in vivo, to induce cell signaling events on a target cell population.

Th17 cells or otherwise cells exhibiting Th17 cell phenotype may have a variety of specific phenotypic properties, depending on the conditions employed. Such phenotypic properties include production of IL-17A and IFNγ. Moreover, cells expanded according to the methods of the invention continue to produce both IL-17A and IFNγ event after their primary expansion. In some instances, cells engaged with ICOS coexpressed both RORγt and T-bet, transcription factors that regulate Th17 and Th1 cell development, respectively. In some instances, umbilical cord T cells engaged with ICOS coexpressed IL-23R and CD161 on their cell surface, phenotypic markers associated with umbilical cord Th17 cells. In some instances, ICOS stimulated cells expressed RORγt.

In one embodiment, the invention provides a purified population of ICOS+CD28+ umbilical cord blood Th17 precursor cells that secret elevated levels of CCL20, IL-17F and IFNγ upon ICOS engagement compared with CD28 engagement. ICOS engagement not only augmented the function of ICOS+CD28+ precursor Th17 cells but also promoted their expansion. This new subset of CD4 cells from umbilical cord blood is believed to be recent thymic emigrants, which express ICOS constitutively, and are imprinted as Th17 cells via ICOS engagement. This new subset of CD4 cells is exhibits inflammatory characteristics with an antitumor capacity. Moreover, the disclosure presented herein demonstrate that ICOS signaling promotes the generation of inflammatory human T cells with an antitumor capacity exceeding those generated with CD28. The cells of the present invention can be used in clinical applications for the design of immunotherapies for patients with cancer, infectious disease and autoimmunity.

T cell populations of the present invention may also be antigen-specific T cells, for example, tumor-antigen-specific T cells. In certain embodiments, antigen-specific T cells can be generated according to the ICOS stimulation methods of the present invention. In certain embodiments, antigen-specific T cells can be administered to a mammal in need thereof as an anti-tumor therapy.

Therapy

The invention encompasses an aAPC wherein the co-stimulatory ligand is a cognate binding partner that specifically binds with a co-stimulatory molecule, as well as where the ligand is an antibody that specifically binds with a costimulatory molecule, and any combination thereof, such that a single aAPC can comprise both nucleic acids encoding costimulatory ligands and/or antibodies specific for costimulatory molecules present on the T cell, and any combination thereof. Preferably, the aAPC comprises a ligand for ICOS. This is because the present invention is based on the surprising discovery that ICOS costimulation rather than CD28 costimulation preferentially expands cells with a Th17 phenotype.

In one embodiment, the invention encompasses using an aAPC that is capable of activating ICOS on a T cell to boost T cells in vivo. For example, the invention includes using ICOSL aAPC to boost T cells in vivo. The T cells may have previously been engineered in vitro and after infusion to a patient, boosted with the ICOSL aAPC vaccination. Alternatively, the ICOSL aAPC may be loaded with antigens and used as a priming vaccine to stimulate a Th17 response.

In another aspect of the invention, a method of activating antigen specific T cells is provided. The method comprises culturing T cells with a first agent that is capable of providing a primary activation signal to the T cell (e.g., anti-CD3 antibody) and a second agent that is capable of activating ICOS on the T cell (anti-ICOS antibody). Preferably, the T cells are cultured in the presence of Th17 polarizing cytokines when the T cells are stimulated with a first agent that is capable of providing a primary activation signal to the T cell (e.g., anti-CD3 antibody) and a second agent that is capable of activating ICOS on the T cell (anti-ICOS antibody). The ICOS stimulated T cells are then genetically redirected with a desired chimeric antigen receptor that recognizes a tumor antigen. Thus, one embodiment of the invention includes generating an ICOS stimulated T cell population prior to contacting the T cell with an antigen.

In certain embodiments, a population of T cells is first contacted with antigen, and then subjected to ICOS stimulation according to the invention. In one particular embodiment, the antigen-specific T cells are induced by vaccination of a patient with a particular antigen, either alone or in conjunction with an adjuvant or pulsed on dendritic cells. Antigen-specific cells for use in expansion using the ICOS stimulation method of the invention may also be generated in vitro.

Another aspect of the present invention provides a method for expanding antigen specific T cells, comprising contacting a population of T cells with an antigen for a time sufficient to induce activation of T cells specific to said antigen; contacting said population of antigen-specific T cells ex vivo according to the ICOS stimulation method of the invention under conditions and for time sufficient to induce proliferation of T cells specific to said antigen, thereby expanding antigen-specific T cells. In one embodiment, the antigen is a tumor antigen. In another embodiment, the antigen is pulsed on or expressed by an antigen-presenting cell. In a further embodiment the population of T cells is contacted with said antigen in vivo. In yet another embodiment, the population of T cells is contacted with said antigen ex vivo. In another embodiment, the method comprises at least one round of peptide-MHC tetramer sorting of said antigen-specific T cells. In certain embodiments, the method of the present invention further comprises at least one round of peptide-MHC tetramer magnetic selection of said antigen-specific T cells.

Another aspect of the present invention provides a method for the treatment of cancer comprising administering to a cancer patient antigen-specific T cells expanded according to the methods provided herein.

The cells generated according to the present invention can also be used to treat autoimmune diseases. Examples of autoimmune disease include but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

The cells generated according to the present invention can also be used to treat inflammatory disorders. Examples of inflammatory disorders include but are not limited to, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

The present invention also provides methods for preventing, inhibiting, or reducing the presence of a cancer or malignant cells in an animal, which comprise administering to an animal an anti-cancer effective amount of the anti-tumor cells of the invention.

The cancers contemplated by the present invention, against which the immune response is induced, or which is to be prevented, inhibited, or reduced in presence, may include but are not limited to melanoma, non-Hodgkin's lymphoma, Hodgkin's disease, leukemia, plasmocytoma, sarcoma, glioma, thymoma, breast cancer, prostate cancer, colo-rectal cancer, kidney cancer, renal cell carcinoma, pancreatic cancer, esophageal cancer, brain cancer, lung cancer, ovarian cancer, cervical cancer, multiple myeloma, hepatocellular carcinoma, nasopharyngeal carcinoma, ALL, AML, CML, CLL, and other neoplasms known in the art.

Alternatively, compositions as described herein can be used to induce or enhance responsiveness to pathogenic organisms, such as viruses, (e.g., single stranded RNA viruses, single stranded DNA viruses, double-stranded DNA viruses, HIV, hepatitis A, B, and C virus, HSV, CMV, EBV, HPV), parasites (e.g., protozoan and metazoan pathogens such as Plasmodia species, *Leishmania* species, *Schistosoma* species, *Trypanosoma* species), bacteria (e.g., Mycobacteria, *Salmonella*, Streptococci, *E. coli*, Staphylococci), fungi (e.g., *Candida* species, *Aspergillus* species) and *Pneumocystis carinii*.

The immune response induced in the animal by administering the subject compositions of the present invention may include cellular immune responses mediated by CD8+ T cells, capable of killing tumor and infected cells, and CD4+ T cell responses. Humoral immune responses, mediated primarily by B cells that produce antibodies following activation by CD4+ T cells, may also be induced. A variety of techniques may be used for analyzing the type of immune responses induced by the compositions of the present invention, which are well described in the art; e.g., Coligan et al., Current Protocols in Immunology, John Wiley & Sons Inc., 1994.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient. It can generally be stated that a pharmaceutical composition comprising the subject cells of the invention, may be administered at a dosage to be determined during appropriate clinical trials. Cells of the invention may also be administered multiple times at these dosages. The optimal dosage and treatment regime for a particular patient can readily be determined by one skilled in the art of medicine by monitoring the patient for signs of disease and adjusting the treatment accordingly.

Cells of the invention can be administered in dosages and routes and at times to be determined in appropriate clinical trials. Cell compositions may be administered multiple times at dosages within these ranges. The cells of the invention may be combined with other methods. The cells of the invention for administration may be autologous, allogeniec or xenogenic to the patient undergoing therapy. If desired, the treatment may also include administration of mitogens (e.g., PHA) or lymphokines, cytokines, and/or chemokines (e.g., GM-CSF, IL-4, IL-13, Flt3-L, RANTES, MIP1-α, etc.) as described herein to enhance induction of the immune response.

The administration of the cells of the invention may be carried out in any convenient manner. The cells of the present invention may be administered to a patient subcutaneously, intradermally, intramuscularly, by intravenous (i.v.) injection, or intraperitoneally. In some instances, the cells of the invention are administered to a patient by intradermal or subcutaneous injection. In other instances, the cells of the invention are administered by i.v. injection. In other instances, the cells of the invention are injected directly into a tumor or lymph node.

The cells of the invention can also be administered using any number of matrices. The present invention utilizes such matrices within the novel context of acting as an artificial lymphoid organ to support, maintain, or modulate the immune system, typically through modulation of T cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized, as such these patents are incorporated herein by reference in their entirety. Matrices comprise features commonly associated with being biocompatible when administered to a mammalian host. Matrices may be formed from natural and/or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release of seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

In one aspect of the present invention, the cells of the invention can be used in vivo as an adjuvant as described in U.S. Pat. No. 6,464,973. In a further embodiment, the cells of the invention can be used as a vaccine to induce an immune response in vivo against an antigen of interest such as those described herein (e.g., tumor antigens, viral antigens, autoantigens, etc). In one embodiment the cells of the invention can be used to generate an immune response in vivo, either administered alone or in combination with other immune regulators and in combination with other known therapies.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Human T helper 17 (Th17) cells regulate host defense, autoimmunity, and tumor immunity. Although cytokines that control human Th17 cell development have been identified, the costimulatory molecules important for Th17 cell generation are unknown. The present invention is partly based on the discovery that the inducible costimulator (ICOS) was critical for the differentiation and expansion of human Th17 cells. Human cord blood contained a subset of CD161+ CD4+ T cells that were recent emigrants from the thymus, expressed ICOS constitutively, and were imprinted as Th17 cells through ICOS signaling. ICOS stimulation induced c-MAF, RORC2, and T-bet expression in these cells, leading to increased secretion of interleukin-21 (IL-21), IL-17, and interferon-γ (IFN-γ) compared with cells stimulated with CD28. Conversely, CD28 ligation abrogated ICOS costimulation, dampening RORC2 expression while promoting the expression of the aryl hydrocarbon receptor, which led to reduced secretion of IL-17 and enhanced production of IL-22 compared with cells stimulated with ICOS. Moreover, ICOS promoted the robust expansion of IL-17+IFN-γ+ human T cells, and the antitumor activity of these cells after adoptive transfer into mice bearing large human tumors was superior to that of cells expanded with CD28. The therapeutic effectiveness of ICOS-expanded cells was associated with enhanced functionality and engraftment in vivo. These findings reveal a vital role for ICOS signaling in the generation and maintenance of human Th17 cells and suggest that components of this pathway could be therapeutically targeted to treat cancer or chronic infection and, conversely, that interruption of this pathway may have utility in multiple sclerosis and other autoimmune syndromes. These findings have provided the rationale for designing new clinical trials for tumor immunotherapy.

The materials and methods employed in the experiments disclosed herein are now described.
Cell Purification Blood samples were obtained from the Human Immunology Core of the University of Pennsylvania. Peripheral blood CD4+ T cells were negatively isolated and >95% pure adult subsets of TH1, TH2, Th17, Treg, and TFH CD4+ T cells were further purified as described (Acosta-Rodriguez et al., 2007 Nat. Immunol. 8:639-646; Liu et al., 2006 J. Exp. Med. 203:1701-1711; Rasheed et al., 2006 Eur. J. Immunol. 36:1892-1903).
T Cell Activation with Beads or aAPCs For stimulation, 1×106 CD4+ T cells were cultured with either 3×106 activating beads coated with antibodies to CD3, CD28, and/or ICOS or with 0.5×106 CD32-transduced aAPCs bearing CD80, CD86, CD70, ICOSL, OX40L, or 4-1BBL. The methods of aAPC generation and T cell expansion are described elsewhere (Parry et al., 2009 J. Immunol. 171:166-174; Suhoski et al., 2007 Mol. Ther. 15:981-988). Cultures were monitored for cell volume and enumerated via Coulter Multisizer 3 (Beckman Coulter).
Cell Culture and TH1, TH2, Th17, and Treg Cell Polarization Cells were cultivated in RPMI 1640 culture media as described previously in a 37° C. and 5% CO2 incubator (Turka et al., 1990 J. Immunol. 144:1646-1653). For polarization experiments, cells were seeded with antibody-coated beads or aAPCs. IL-2 (50 to 100 IU/ml) was added at day 3 and media were replaced as described previously (Suhoski et al., 2007 Mol. Ther. 15:981-988; Maus et al., 2002 Nat. Biotechnol. 20:143-148). For Th17 cell polarization, as indicated, IL-1b (10 ng/ml), IL-6 (10 ng/ml), IL-23 (20 ng/ml), and neutralizing antibodies (10 mg/ml) against IL-4 and IFN-γ (eBioscience) were added at day 0 and maintained throughout the experiment. Experiments were conducted with fetal calf serum containing endogenous sources of TGF-β. In experiments indicated, IL-21 (25 ng/ml) (eBioscience) and an antibody to IL-2 (5 mg/ml) (R&D Systems) were added to Th17-polarized T cells.

For TH1 cell polarization, IL-12 (5 ng/ml) and neutralizing antibodies against IL-4 (eBioscience) were added at day 0. For TH2 cell polarization, IL-4 (5 ng/ml) and neutralizing antibodies against IFN-γ (eBioscience) were added at day 0 and maintained throughout the experiment. For Treg cell polarization, TGF-β (5 ng/ml) and rapamycin (50 ng/ml) were added at day 0 and maintained throughout the experiment. Cells and supernatant were harvested at various days throughout short- and long-term primary and secondary cultures for intracellular staining and/or ELISA.
Real-Time Polymerase Chain Reaction RNA was extracted with the RNAqueous isolation kit (Ambion), and then complementary DNA (cDNA) was transcribed with iScript cDNA Synthesis (Bio-Rad) and used as a template for Taqman polymerase chain reaction (PCR) from the specified samples. Expression of RORC2, Tbx21 (T-bet), FoxP3, AHR, c-MAF, IL-17A, IL-21, and IL-23R was assessed with specific primers and probes (Applied Biosystems) via the Applied Biosystems 7500 Fast System. Gene expression was normalized to expression of the human gene b-actin. Relative quantitation was performed with unmanipulated CD4+ T cells as a reference.
Surface and Intracellular Staining For intracellular cytokine staining, cells were incubated for 5 hours with PMA (20 ng/ml) (Sigma) and ionomycin (2 mg/ml) (Sigma) and GolgiStop (BD). Surface staining was performed, followed by intracellular staining, as described previously, with an LSR II (BD Biosciences) flow cytometer and FlowJo software (Tree Star Inc.). RORC2, T-bet, and FoxP3 were stained with FoxP3 staining buffers (eBioscience).
Mice The University of Pennsylvania Institutional Animal Care and Use Committee approved all animal experiments. NSG mice were purchased from The Jackson Laboratory and bred in the vivarium at the University of Pennsylvania. The mice were housed under specific pathogen-free conditions in microisolator cages and given ad libitum access to autoclaved food and acidified water.

In Vivo Assessment of Anti-Mesothelin CAR T Cells

A chimeric anti-mesothelin single-chain variable fragment (scFv) fusion protein containing the 4-1BB and T cell receptor z (TCRz) signaling domains was generated as described previously (Carpenito et al., 2009 Proc. Natl. Acad. Sci. U.S.A. 106:3360-3365). M108 xenograft tumors were established as described previously (Carpenito et al., 2009 Proc. Natl. Acad. Sci. U.S.A. 106:3360-3365) in NSG mice before adoptive transfer of Th17 cells. Tumors were measured with calipers, and their area was calculated by multiplying the length by the width.

Statistical Analysis

Tumor growth data were analyzed by life table methods with a linear mixed-effects model via a conservative Bonferroni correction approach. Values of P<0.005 were considered statistically significant. Other data were analyzed by analysis of variance (ANOVA) Scheffe test or Student's t test. Values of P=0.05 were considered statistically significant.

The results of the experiments disclosed herein are now described.

Example 1: ICOS and CD28 have Distinct Effects on Human CD4+ T Cell Subsets

ICOS was originally identified as a molecule expressed on T cells only after activation (Hutloff et al., 1999 Nature 397:263-266). Constitutive expression of ICOS was later found on a subpopulation of resting murine effector memory T cells, Treg cells, and follicular helper T (TFH) cells (Burmeister et al., 2008 J. Immunol. 180:774-782; Ito et al., 2008 Immunity 28:870-880; King et al., 2008 Annu Rev. Immunol. 26:741-766). Given the recent identification of human Th17 cells, experiments were designed to examine whether ICOS was also constitutively expressed on these cells. Resting peripheral blood CD4+ T cells were sorted into various subsets based on their expression of chemokine receptors and other cell surface molecules. This strategy yielded TH1 (CXCR3+CCR4−CCR6−), TH2 (CCR4+CXCR3−CCR6−), Th17 (CCR4+CCR6+), Treg (CD25+CD127lo), and TFH (CXCR5+CD45RO+) subsets (Acosta-Rodriguez et al., 2007 Nat. Immunol. 8:639-646; Liu et al., 2006 J. Exp. Med. 203:1701-1711; Rasheed et al., 2006 Eur. J. Immunol. 36:1892-1903). Surprisingly, 40% of cells in the Th17 subset constitutively expressed ICOS, whereas the TH1 and TH2 subsets did not express ICOS (FIGS. 1A and 1B). As expected, Treg and TFH subsets constitutively expressed ICOS (Burmeister et al., 2008 J. Immunol. 180: 774-782; Ito et al., 2008 Immunity 28:870-880; King et al., 2008 Annu Rev. Immunol. 26:741-766), whereas all subsets constitutively expressed CD28 at high levels (FIGS. 1A and 1B).

Given that human T cell subsets constitutively express varying amounts of ICOS and CD28, the next set of experiments was designed to evaluate the functional effects of signaling via these particular molecules on each subset. Thus, subsets were sorted as described above and then stimulated with antibodies to CD3/CD28 or CD3/ICOS beads. IL-2, IL-4, interferon-γ (IFN-γ), IL-10, IL-22, IL-17A, IL-17F, CCL20, and IL-21 production was measured by enzyme-linked immunosorbent assay (ELISA) (FIG. 1C).

As expected, all subsets except Treg cells secreted substantial amounts of IL-2 after CD28 costimulation (FIG. 1C, i). In contrast, ICOS costimulation did not trigger IL-2 secretion, corroborating previous finding that CD28, but not ICOS, mediates IL-2 production by T cells (Riley et al., 2005 Blood 105:13-21; Parry et al., 2009 J. Immunol. 171:166-174). Furthermore, CD28, but not ICOS, induced IL-4 production by TH2 cells (FIG. 1C, ii). IL-10 and IL-22 secretion was triggered by both CD28 and ICOS costimulation in a subset-specific manner, although in most subsetsCD28 costimulation induced higher amounts of these cytokines (FIG. 1C, iv and v). In contrast, ICOS costimulation of Th17 cells resulted in significantly higher production of IL-17A, IL-17F, CCL20, and IL-21 compared with CD28 costimulation (FIG. 1C, vi to ix). Notably, ICOS-stimulatedTh17 cells also produced greater amounts of IFN-γ than CD28-stimulated TH1 cells, a subset reported to be a dominant source of IFN-γ secretion (FIG. 1C, iii). Although ICOS costimulation augments Th17 cell function, it is interesting that this signal did not amplify TH1 or TH2 cell function, likely because these cells lack ICOS.

Example 2: ICOS Drives Human Th17 Cell Differentiation

Costimulatory molecules play critical roles in initiating T cell responses (Greenwald et al., 2005 Annu Rev. Immunol. 23:515-548; Smith et al., 1994 Cell 76:959-962), but their individual influence on human Th17 functionality remains unknown. To understand their respective impact onTh17 function, peripheral blood CD4+ T cells were activated with OKT3-loaded artificial APCs (aAPCs) engineered to express CD86, CD80, CD70, ICOSL, OX40L, or 4-1BBL and then cultured the cells in Th17-polarizing conditions (IL-6, IL-1b, IL-23, neutralizing IFN-γ, and neutralizing IL-4 antibodies in serum containing endogenous sources of TGF-β). Only ICOS costimulation reproducibly induced IL-17F secretion (FIG. 2A), supporting the notion that ICOS might play a unique role in human Th17 cell development.

Figure 2:
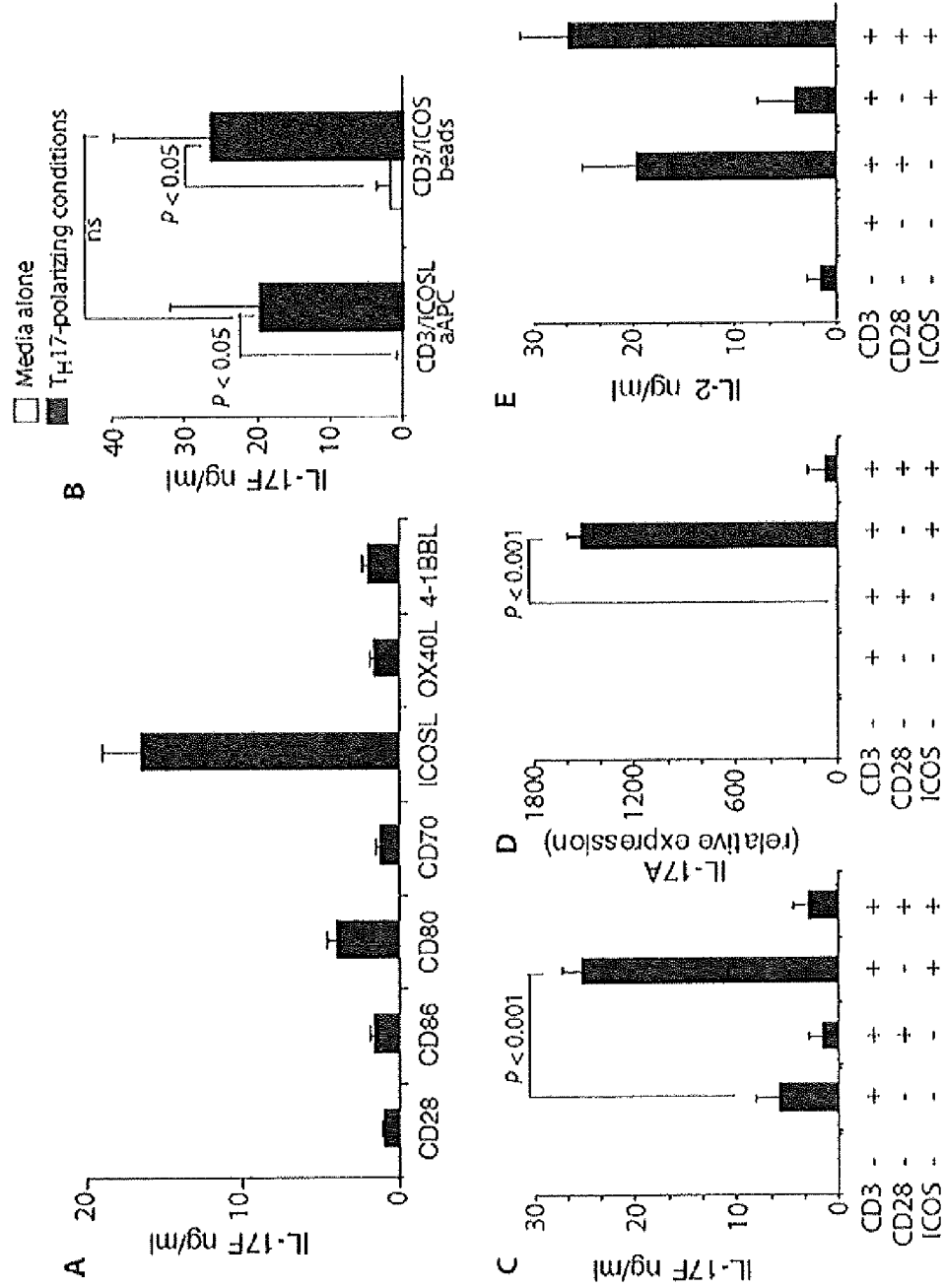
FIG. 2, comprising
Figure 2:
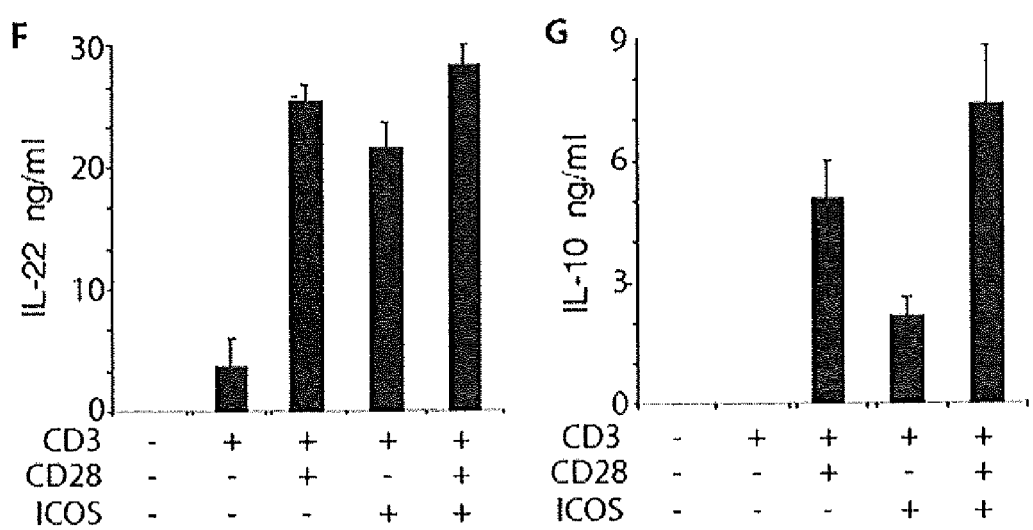

The next set of experiments was designed to assess whether ICOS engagement alone might be sufficient to induce IL-17F secretion by bulk unpolarized CD4+ T cells. It was observed that ICOS engagement was not sufficient to promote significant IL-17F production in the absence of Th17-polarizing conditions. However, in the presence of Th17-polarizing conditions, ICOS induced IL-17F secretion from bulk CD4+ T cells (FIG. 2B). Delivery of the ICOS signal via either beads or aAPCs was equally effective at inducing IL-17F secretion (FIG. 2B). Thus, although ICOS was sufficient to augment IL-17F secretion in already differentiated CCR4+CCR6+ Th17 cells (FIG. 1C), it was not capable of inducing IL-17F secretion by bulk CD4+ T cells in the absence of Th17-polarizing conditions (FIG. 2B). This inability to detect IL-17F may be, in part, due to the low frequency of Th17 cells in bulk CD4+ T cells ICOS and CD28 costimulation are both required for the differentiation of murine Th17 cells (Park et al., 2005 Nat. Immunol. 6:1133-1141). Therefore, it is suspected that they would also augment human Th17 function in combination. Conversely, the addition of CD28 with ICOS markedly reduced IL-17F secretion (FIG. 2C) and IL-17A messenger RNA (mRNA) expression (FIG. 2D). Yet, combining these signals did not exert a similar "veto effect" on IL-2, IL-10, or IL-22 secretion (FIG. 2, E to G). These data are surprising given that CD28 is often used to expand human Th17 cells.

Example 3: ICOS Expands the Population of IL-17A+IFN-γ+ Human CD4+ T Cells

Figure 3:
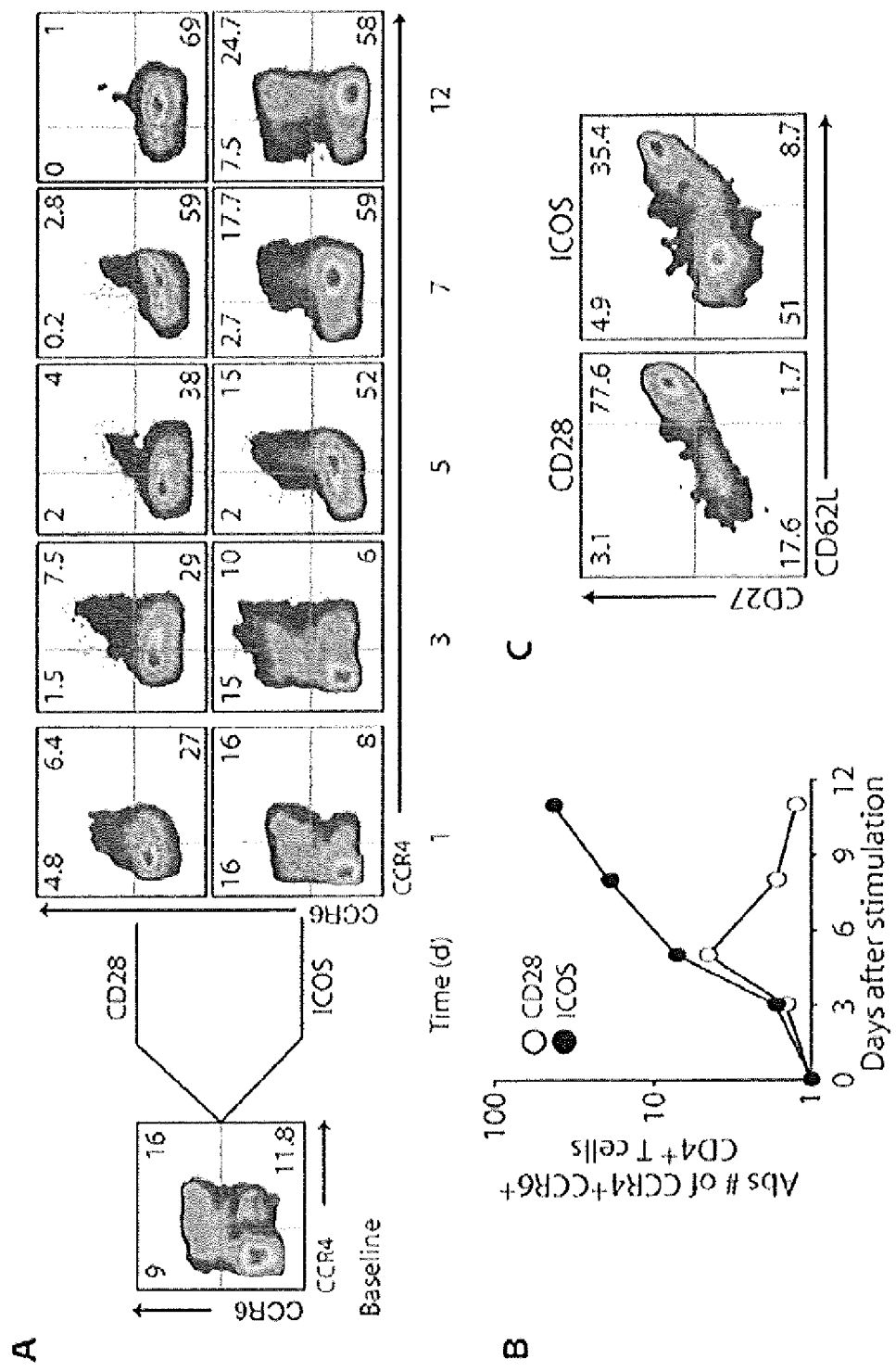
FIG. 3, comprising
Figure 3:
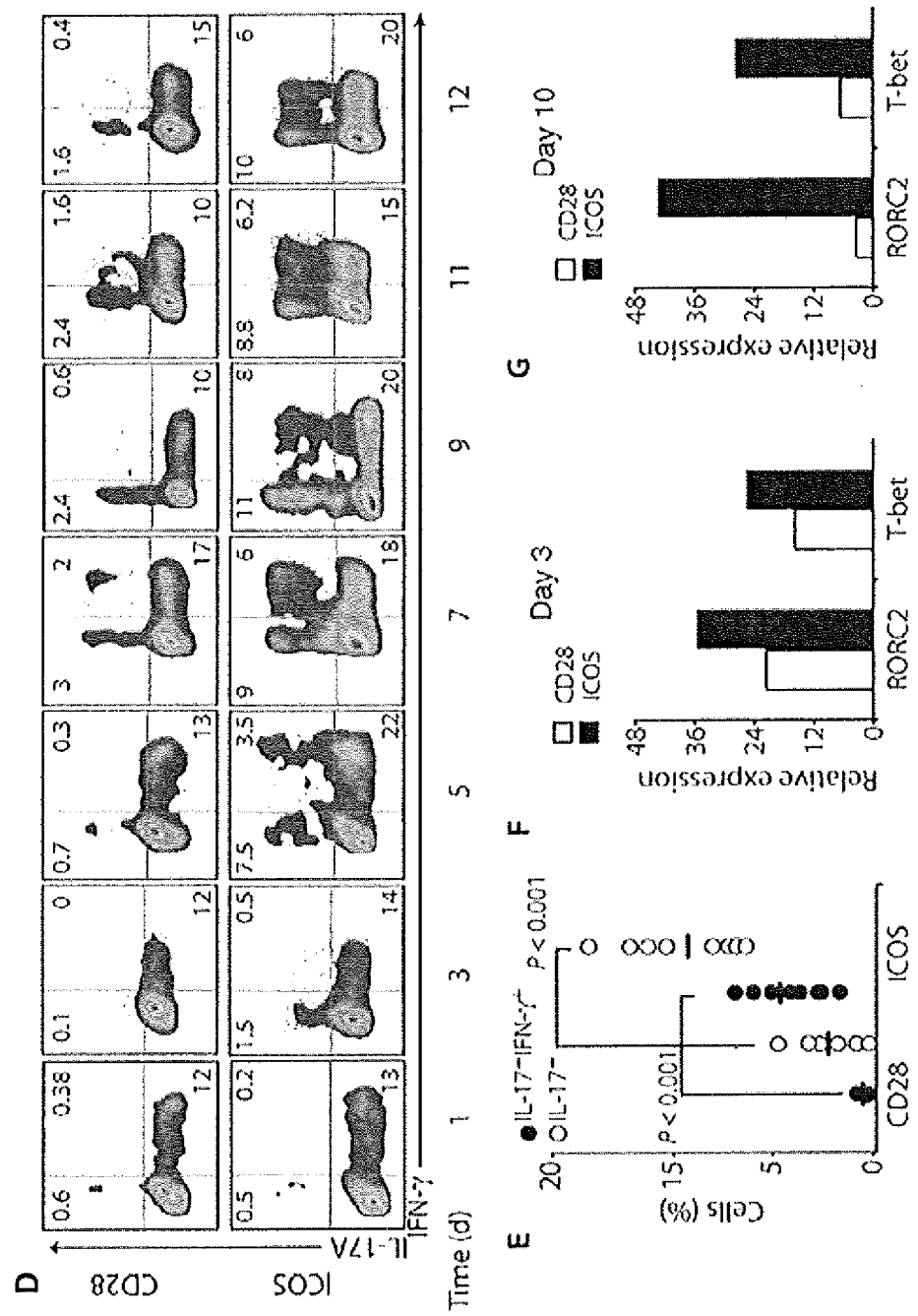

Although ICOS augmented human Th17 cell function at early time points (day 3 after activation), it remained unclear whether ICOS supported their long-term development. To address this question, the frequency and absolute numbers of CCR4+CCR6+CD4+ T cells were measured throughout their primary expansion. At baseline, the frequency of CCR4+CCR6+CD4+ T cells was ~16% (FIG. 3A). However, a progressive decrease in the frequency of these cells was observed in the CD28-costimulated culture. In contrast, the frequency of CCR4+CCR6+CD4+ T cells was stable, and even increased slightly, in the ICOS-costimulated culture. The selective outgrowth of these cells by ICOS was apparent when their absolute numbers were compared to those expanded with CD28 (FIG. 3B). In the ICOS-stimulated culture, the number of CCR4+CCR6+CD4+ T cells increased by more than 30-fold, whereas in the CD28-stimulated culture, their number increased for 5 days and then returned to baseline. Cultures driven by CD28 had a greater frequency of cells with a central memory-like (CD62LhiCD27hi) phenotype, as reported (Bondanza et al., 2006 Blood 107:1828-1836), whereas ICOS-driven cultures contained a higher frequency of cells with an effector memory-like (CD62LloCD27lo) phenotype (FIG. 3C). The next set of experiments was designed to evaluate the effects of CD28 or ICOS on human Th17 cell function over time. In cultures costimulated with CD28, Th17-polarized CD4+ T cells produced IL-17A after the first 5 to 7 days of expansion (FIG. 3D), consistent with previous reports. However, the frequency of CD28-engaged Th17-polarized cells producing IL-17A or both IL-17A and IFN-γ declined nearly to baseline levels by the end of their primary expansion. In contrast, the frequency of these cells increased over time in ICOS-costimulated cultures (FIG. 3D), a finding reproduced in several independent cultures. Cells engaged with ICOS coexpressed both transcription factors RORC2 and T-bet (FIGS. 3F and 3G), master regulators of Th17 and TH1 differentiation, at greater mRNA concentrations than cells engaged with CD28 over time. Thus, ICOS expands the population of IL-17A+IFN-γ+CD4+ T cells (FIG. 3E) and this correlates to induction of RORC2 and T-bet.

Figure 4:
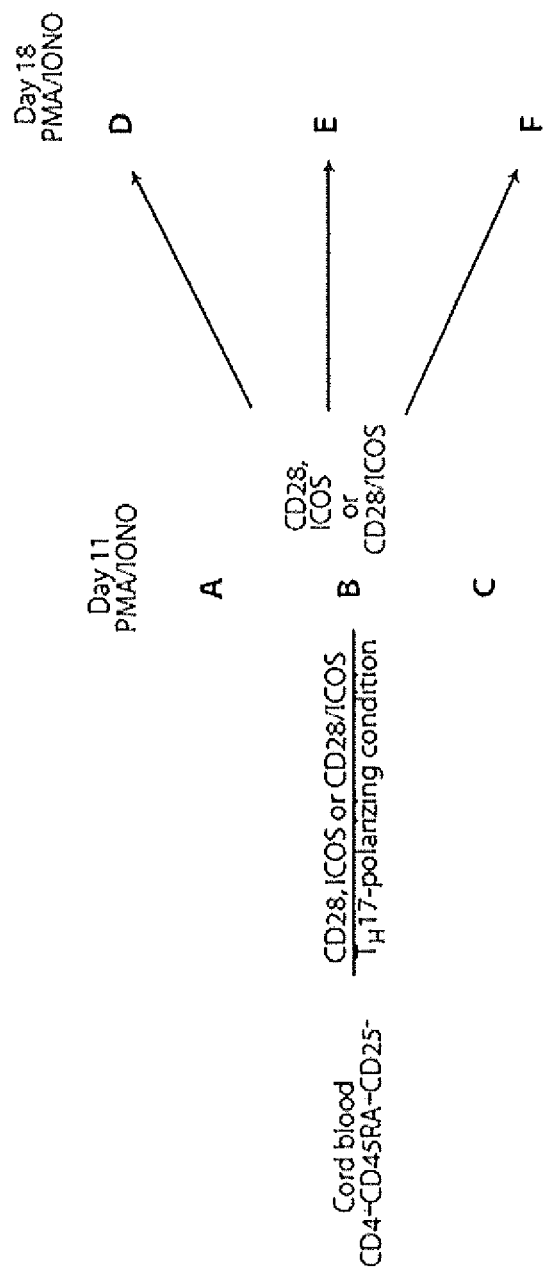
FIG. 4, comprising
Figure 4:
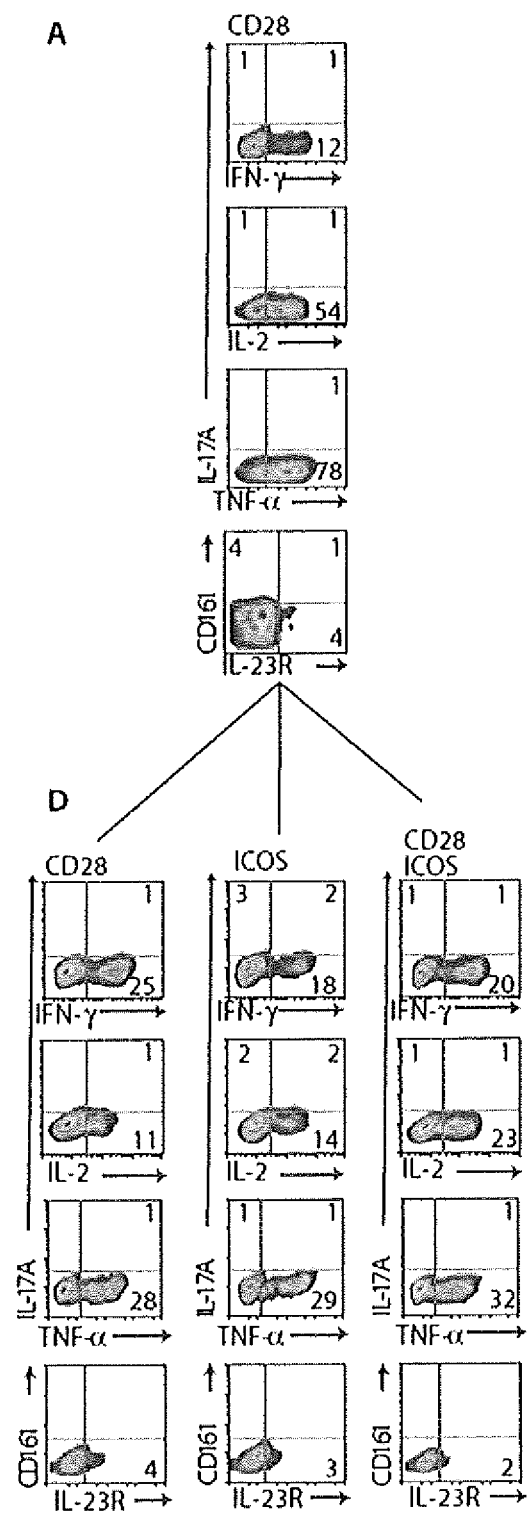
Figure 4:
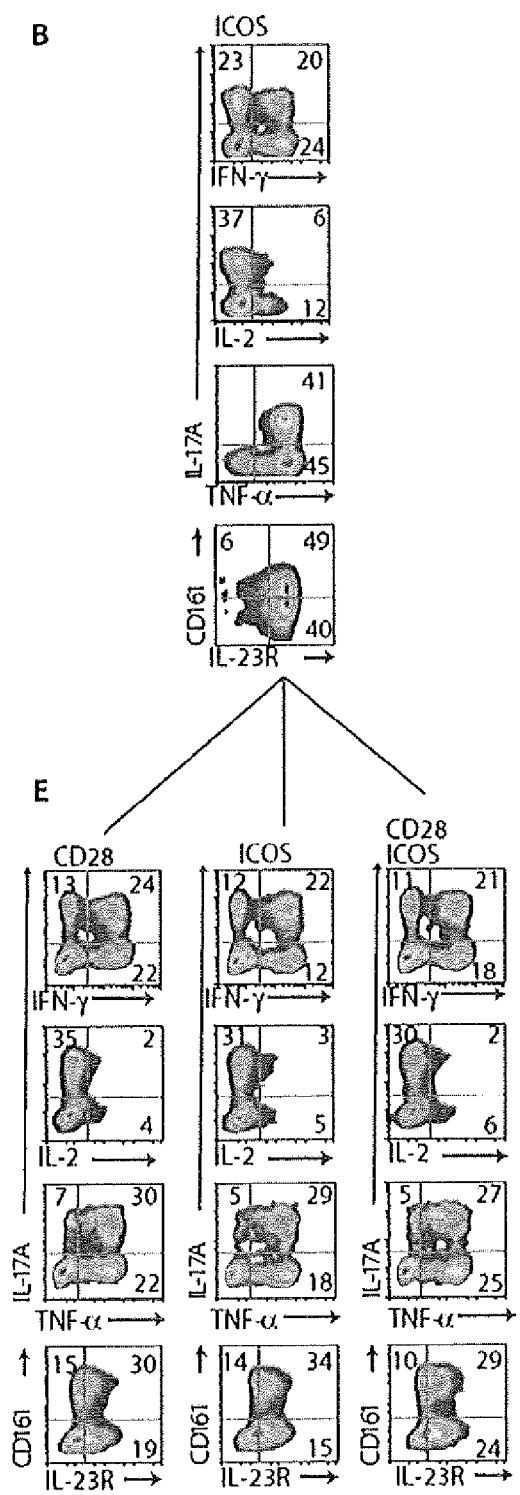
Figure 4:
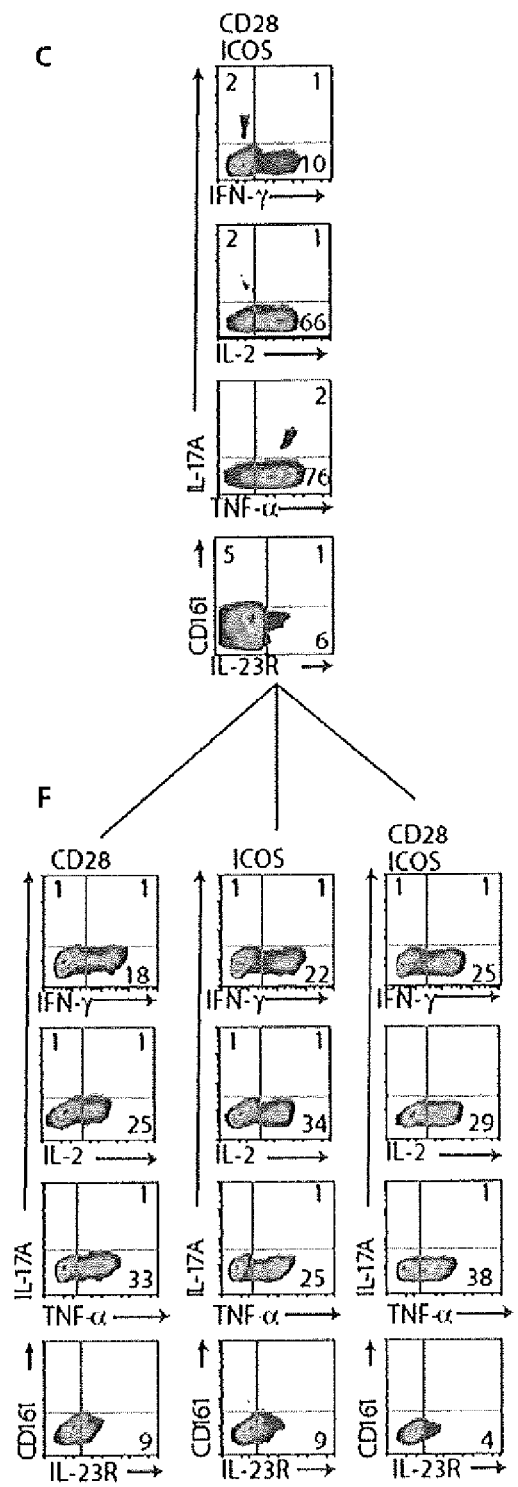
Figure 8:
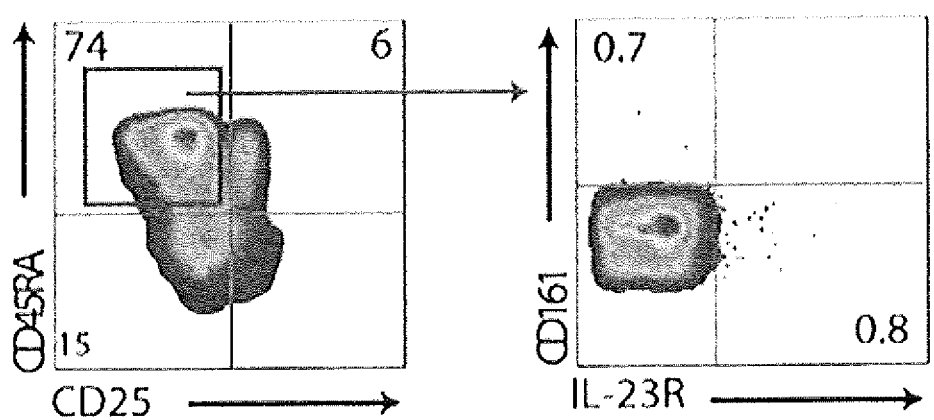
FIG. 8 is an image demonstrating that UCB CD45RA+CD25-CD4+ T cells contain few CD161+IL-23R+ cells. The expression of CD161 and IL-23R surface markers on CD45RA+CD25-CD4+ T cells was assessed on human umbilical cord blood cells using flow cytometry.

Example 4: ICOS and CD28 have Distinct Roles in Development of Th17 Cells Derived from Cord Blood The above data indicated that ICOS preferentially expands effector human Th17 cells, but these data did not discern whether ICOS supports their development from naïve CD4+ T cells. Bauquet and coworkers reported that ICOS was crucial for the expansion but not the development of murine Th17 cells (Bauquet et al., 2009 Nat. Immunol. 10:167-175). Thus, the next set of experiments was designed to determine whether naïve CD4+ T cells preferentially differentiate into Th17 cells via ICOS signaling. To test this, naïve CD45RA+CD25-CD4+ T cells from umbilical cord blood (UCB) were sorted, cultured in Th17-polarizing conditions, and activated with an antibody to CD3 beads bearing antibodies to CD28 and/or ICOS. The function and phenotype of the cultures were assessed after primary (day 11) and secondary (day 18) stimulation (FIG. 4 scheme). IL-17A, IFN-γ, IL-2, and tumor necrosis factor-α (TNF-α) were measured after phorbol 12-myristate β-acetate (PMA)-ionomycin activation. It was observed that >40% of cells engaged with ICOS produced IL-17A alone or IFN-γ alone and that ~20% of ICOS engaged cells secreted both cytokines. In contrast, few cells engaged with CD28 produced IL-17A (FIGS. 4A and 4B). CD28 was indeed functional under these conditions because ~10% of these cells produced IFN-γ and >50% of these cells produced IL-2 after CD28 or CD28 plus ICOS costimulation (FIGS. 4A and 4C). Yet, only ~10% of cells secreted IL-2 after ICOS costimulation alone (FIG. 4B). Combining CD28 with ICOS costimulation prevented IL-17A production, and IFN-γ was produced by these cells at similar levels to CD28 stimulation alone (FIG. 4C). Primary engagement of cells with ICOS but not CD28 induced substantial TNF-α and IL-17A coexpression. CD161 expression was assessed as well, because human Th17 cells originate from CD161+CD4+ T cell precursors in UCB (Cosmi et al., 2008 J. Exp. Med. 205: 1903-1916). Nearly half of cells engaged with ICOS coexpressed CD161 and IL-23 receptor (IL-23R) (FIG. 4B), whereas <5% of cells engaged with CD28 or CD28 plus ICOS were IL-23R– and CD161-positive (FIGS. 4A and 4C) and resting CD4+CD45RA+CD25– T cells contain <0.5% of these cells (FIG. 8). Examination of cells after secondary expansion revealed that cells originally stimulated with ICOS continued to secrete high amounts of IL-17A, IFN-γ, and TNF-α, and this was independent of the mode of secondary costimulation (FIG. 4E). Likewise, ~30% of these cells continued to coexpress IL-23R and CD161. However, virtually no UCB Th17-polarized cells initially stimulated with CD28 or with CD28 plus ICOS secreted IL-17A, even after a restimulation with ICOS (FIGS. 4D and 4F). Thus, CD28 costimulation does not block IL-17A secretion after primary induction by unopposed ICOS costimulation (FIGS. 4B and 4E). These data suggest an important role for ICOS in programming Th17 development from naïve human UCB CD4+ T cells.

Example 5: ICOS Augments Human Th17 Function by Inducing c-MAF and IL-21

Figure 5:
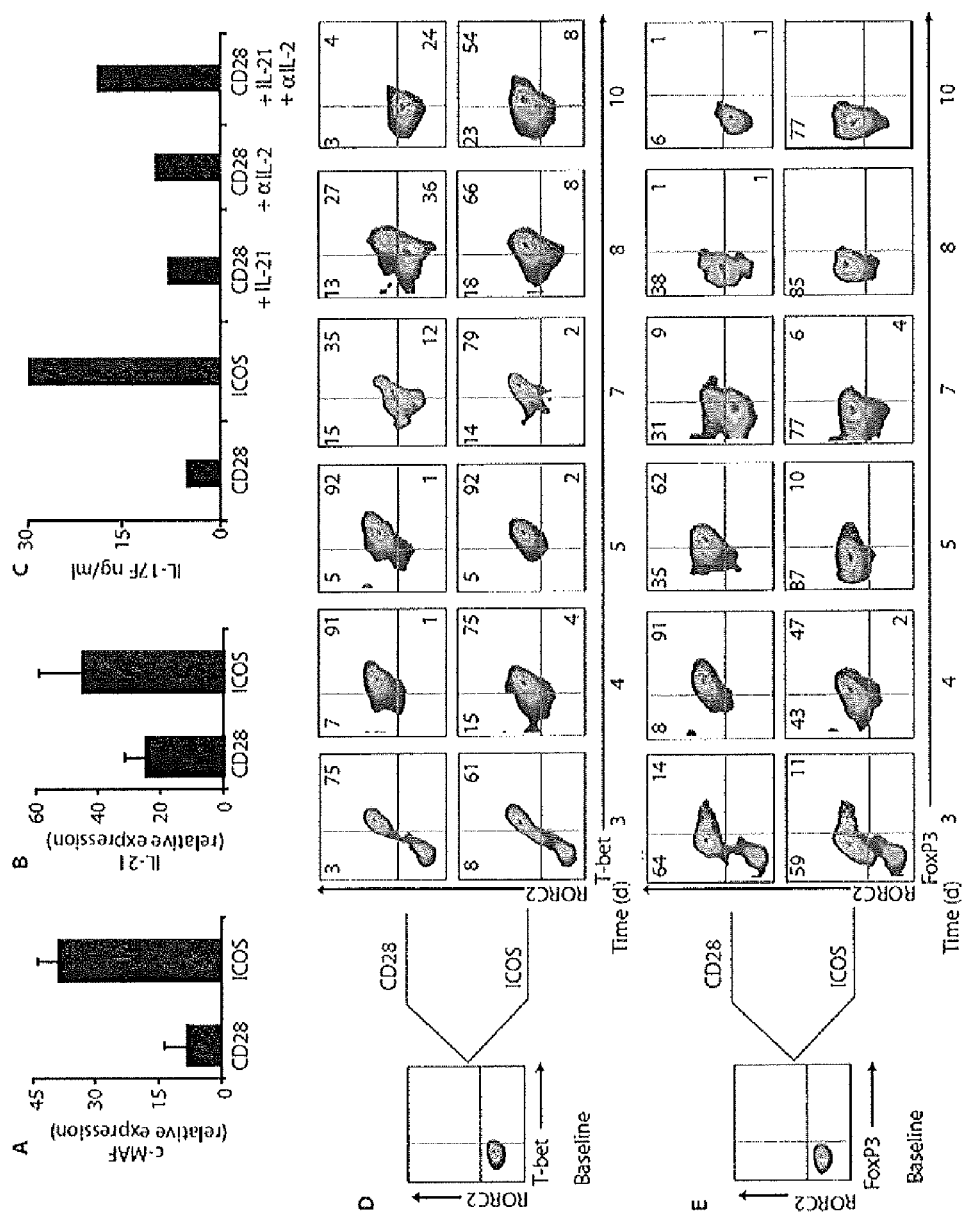
FIG. 5, comprising
Figure 5:
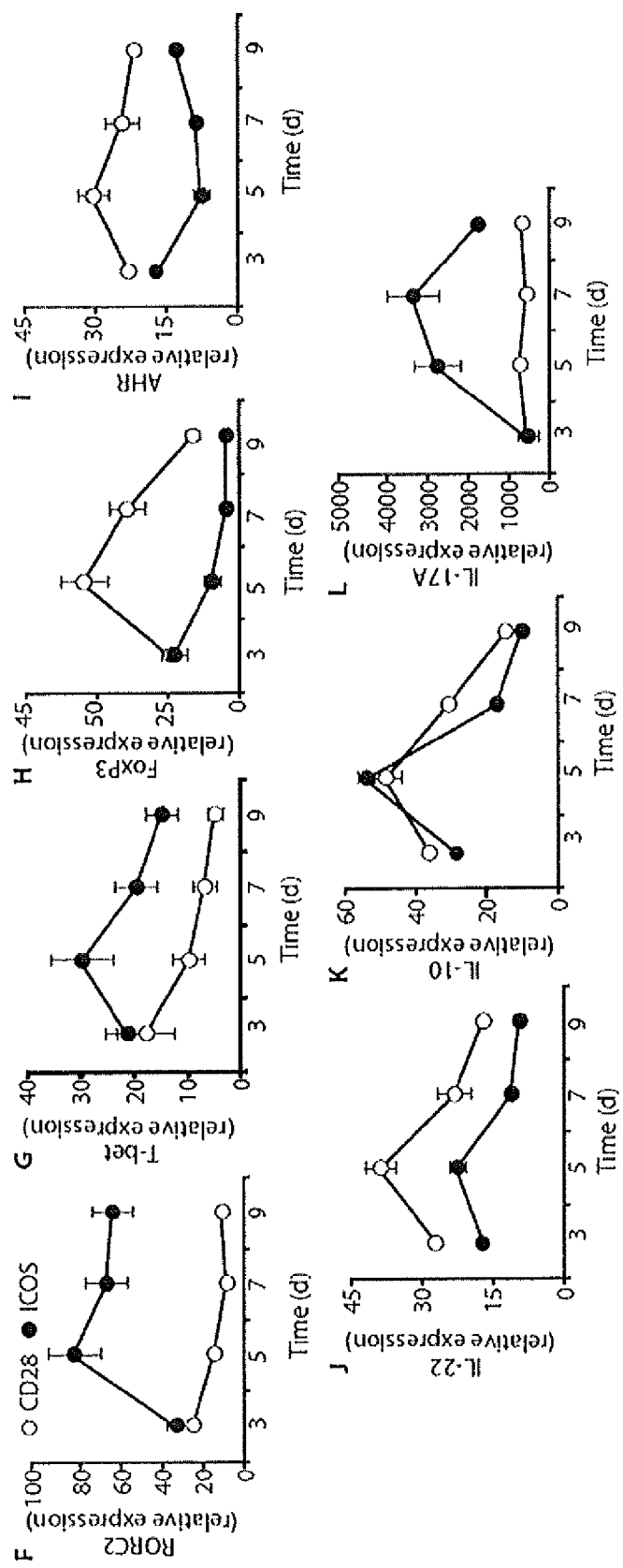
Figure 9:
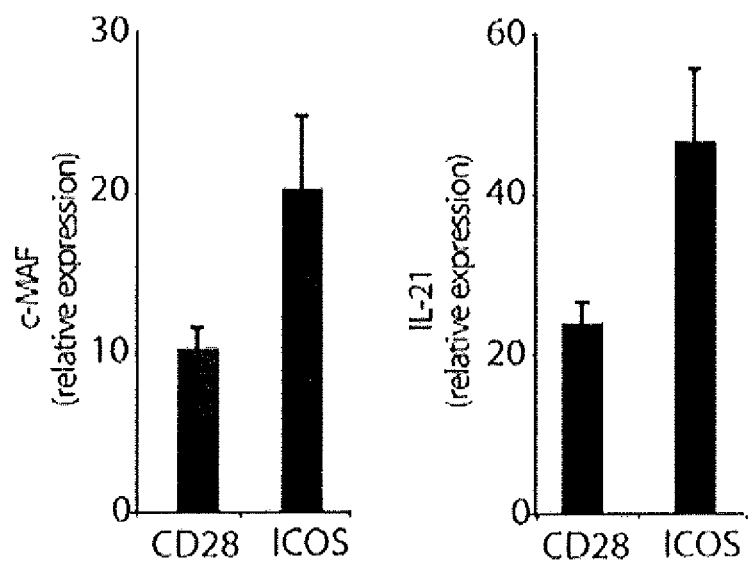
FIG. 9 is an image demonstrating that ICOS induces c-MAF and IL-21. PB CD4+ T cells were cultured in Th17 polarizing conditions (IL-1β, IL-6, IL-23, plus neutralizing anti-IFN-γ and anti-IL-4) and activated with anti-CD3 beads bearing either anti-CD28 or anti-ICOS antibodies. After their primary expansion, their c-MAF and IL-21 expression mRNA levels was assessed by RT-PCR.

The next set of experiments was designed to investigate the mechanisms underlying enhanced human Th17 cell functionality via ICOS. In mice, ICOS induces the transcription factor c-MAF, which, in turn, transactivates IL-21 and augments Th17 function (Bauquet et al., 2009 Nat. Immunol. 10:167-175). The next experiments were performed to evaluate whether ICOS also induces c-MAF in human Th17 cells, given that ICOS increases IL-21 secretion (FIG. 1C, ix). Human UCB CD4+ T cells polarized toward a Th17 phenotype expressed considerably higher mRNA concentrations of c-MAF and IL-21 upon ICOS versus CD28 costimulation (FIGS. 5A and 5B). Similar results were observed in peripheral blood human Th17 cells (FIG. 9). Thus, ICOS induced greater amounts of c-MAF expression than CD28, corresponding with increased IL-21 expression by ICOS-stimulated human Th17 cells. Without wishing to be bound by any particular theory, it is believed that IL-21 induced by ICOS was partially responsible for enhanced human Th17 cell functionality. Thus, it was assessed whether adding exogenous IL-21 to CD28-stimulated Th17-polarized UCB CD4+ T cells would increase their potential to secrete IL-17F.

Consistent with previous studies (Yang et al., 2008 Nature 454:350-352), adding IL-21 to CD28-stimulated Th17-polarized UCB cells modestly increased their capacity to secrete IL-17F but not to the level attained by ICOS-stimulated Th17-polarized UCB cells (FIG. 5C). Given that Th17 cells costimulated with CD28 secrete significantly higher amounts of IL-2 than those stimulated with ICOS, it is believed that IL-2 might be responsible for the reduced functionality observed in CD28-stimulated Th17-polarized UCB cells.

Indeed, IL-17F production was increased in the cultures where IL-2 was neutralized. Furthermore, exogenous IL-21 together with IL-2 neutralization in the culture of CD28-stimulated Th17-polarized UCB cells further increased IL-17F production, but it still did not induce IL-17F secretion to a level comparable to that elicited by ICOS stimulation (FIG. 5C). Thus, in addition to c-MAF-mediated IL-21 production, other factors are likely involved in mediating the ICOS-enhanced function of human Th17-polarized UCB cells.

Example 6: ICOS Induces RORC2 Expression

To better understand the mechanisms underlying how ICOS signaling augmented the functionality of human Th17 cells, experiments were performed to investigate how ICOS regulates the cell expression of RORC2 (RORgt), T-bet (Tbx21), and FoxP3, master regulators of Th17, TH1, and Treg cells (Zhu et al., 2010 Annu Rev. Immunol. 28:445-489), respectively. Thus, RORC2, T-bet, and FoxP3 were measured in naïve UCB CD25−CD4+ T cells cultured in Th17-polarizing conditions over time via flow cytometry. At baseline, the cells expressed virtually no RORC2, T-bet, or FoxP3; there was a transient activation-associated increase in their expression in each culture at 3 to 5 days after stimulation (FIGS. 5D and 5E). However, by the end of their primary expansion, it was observed that >75% of ICOS-stimulated cells expressed RORC2 (FIGS. 5D and 5E, days 7 to 10). In contrast, the frequency of CD28-expanded cells expressing RORC2, T-bet, and FoxP3 progressively declined (FIGS. 5D and 5E). Likewise, ICOS induced greater mRNA expression of RORC2 and T-bet than CD28 (FIGS. 5F and 5G), whereas CD28 induced greater yet transient mRNA expression of FoxP3 than ICOS in these cells (FIG. 5H).

Figure 10:
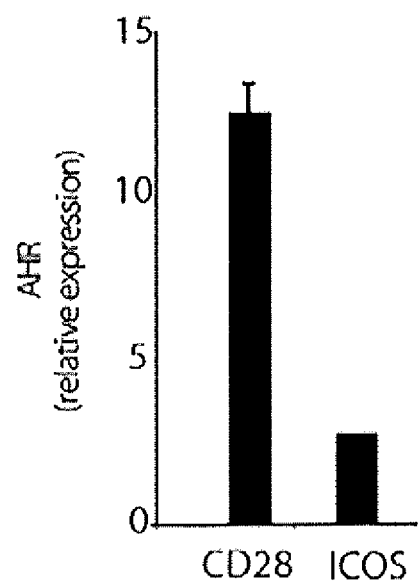
FIG. 10 is an image demonstrating that CD28 induces expression of the aryl hydrocarbon receptor. PB CD4+ T cells were programmed toward a Th17 phenotype and activated with anti-CD3 beads bearing either anti-CD28 or anti-ICOS antibodies. After their primary expansion, their mRNA expression level of AHR relative to β-actin was assessed by RT-PCR.

Similar to peripheral blood data (FIG. 2F and FIG. 10), CD28 induced higher expression of the AHR transcripts than ICOS (FIG. 5I), likely resulting in their heightened production of IL-22 (FIG. 5J). These data are consistent with findings in mice showing that AHR correlates with IL-22 production by T cells (Veldhoen et al., 2009 J. Exp. Med. 206:43-49; Veldhoen et al., 2008 Nature 453:106-109). IL-10 expression was comparable in cells stimulated with either CD28 or ICOS (FIG. 5K), whereas IL-17A expression was significantly higher in cells stimulated with ICOS versus CD28 over time (FIG. 5L). RORC2 transcripts were stably induced at high amounts throughout the culture compared to T-bet and FoxP3 transcripts in cells stimulated with ICOS (FIGS. 5F to 5H).

Figure 11:
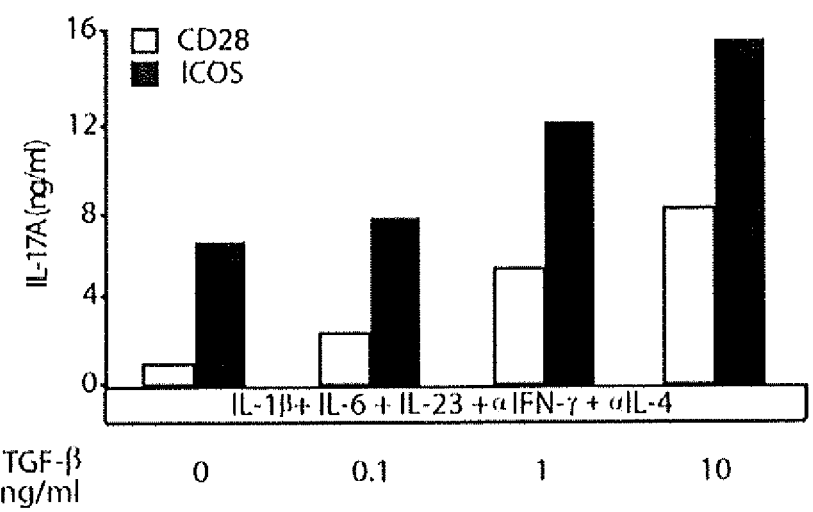
FIG. 11 is an image demonstrating that exogenous TGF-β augments the inflammatory potential of human TH 17 cells. PB CD4+ T cells were programmed toward a TH 17 phenotype and activated with anti-CD3 beads bearing either anti-CD28 or 2 anti-ICOS antibodies in media containing serum and the indicated supplemental TGF-β (from 0.1-10 ng/ml) was added to the culture on day 1. IL-17 A secretion by cells was measured on day 5 post-activation by ELISA.

Without wishing to be bound by any particular theory, it is believed that the amounts of IL-17A with CD28 costimulation might be low because the cells were differentiated in serum without the addition of TGF-β. Indeed, titrating TGF-β into the culture over a 3-log 10 range of concentration increased the amount of IL-17A produced by Th17-polarized CD4+ T cells expanded with the CD28 signal but not to the amounts reached by ICOS-stimulated cells (FIG. 11). These data underscore the notion that CD28-costimulated T cells are composed of Th17 cells that have not reached their full inflammatory potential. Further, they reveal the importance of the availability of TGF-β in the microenvironment as well as CD28 "veto signaling" (FIGS. 2C and 2D), which have the potential to regulate the inflammatory potential of Th17 cells.

Example 7: UCB CD161+CD4+ T Cells Constitutively Express ICOS

Figure 6:
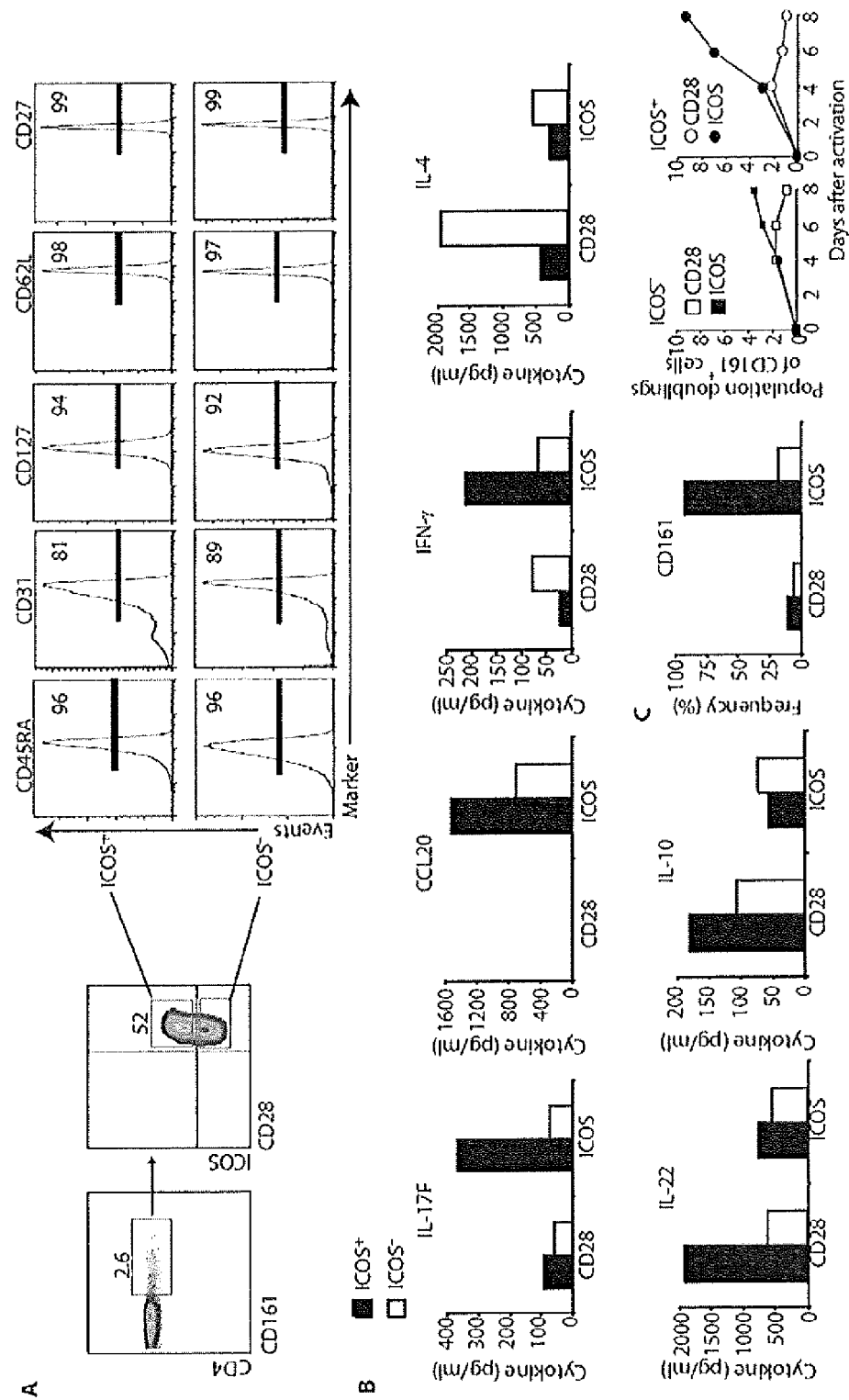
FIG. 6, comprising
Figure 6:
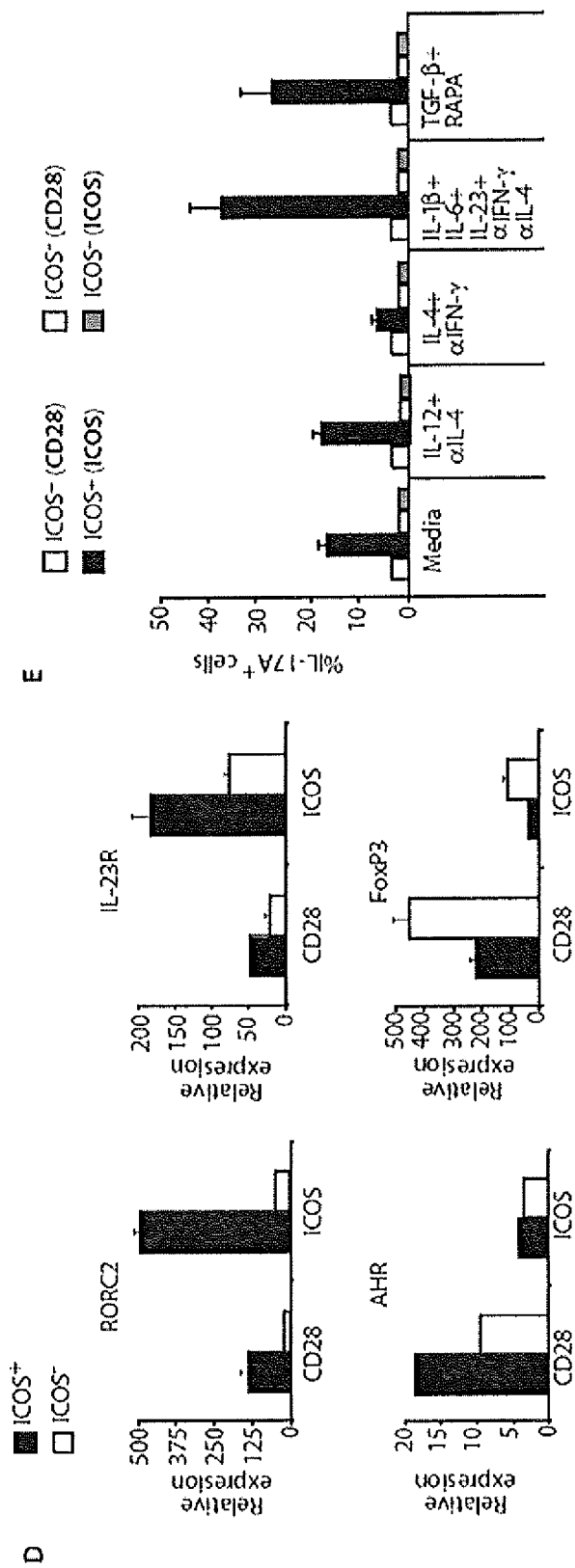

Given that Th17 cells originate from a CD161+CD4+ UCBT cell precursor (Cosmi et al., 2008 J. Exp. Med. 205:1903-1916) and that ICOS is critical for augmenting their function, experiments were performed to investigate whether these cells express ICOS constitutively. Similar to peripheral blood CCR4+CCR6+CD4+ Th17 cells (FIGS. 1A and 1B), ~50% of resting CD161+CD4+ cord blood T cells expressed ICOS (FIG. 6A). Thus, the next experiments were performed to investigate whether CD161+CD4+ T cells that constitutively express ICOS were phenotypically different from ICOS−CD161+CD4+ T cells.

Given that ICOS+ cells from peripheral blood are largely effector memory cells, it was hypothesized that ICOS+ CD161+CD4+ cord blood T cells would be a more differentiated subset than ICOS−CD161+CD4+ T cells. Unexpectedly, ICOS+CD161+CD4+ and ICOS−CD161+CD4+ T cells shared a similar naïve phenotype (FIG. 6A), as indicated by comparable high expression of CD45RA, CD127, CD62L, and CD27, and bright expression of CD31, which is typical of recent thymic emigrants (Köhler et al., 2009 Blood 114:290-298).

Example 8: ICOS+CD161+CD4+ T Cells are Imprinted as Th17 Cells Via ICOS Signaling The next set of experiments was designed to investigate whether CD161+CD4+ cord blood T cells that express ICOS differentiate into human Th17 cells via ICOS signaling. Thus, experiments were performed to examine the function of ICOS+CD161+CD4+ versus ICOS−CD161+CD4+ T cells sorted from UCB that were stimulated with antibodies to either CD3/CD28 or CD3/ICOS beads under Th17-polarizing conditions.

ICOS+CD161+CD4+ T cells secreted higher amounts of IL-17F, CCL20, and IFN-γ upon ICOS engagement compared to ICOS−CD161+CD4+ T cells (FIG. 6B). In contrast, CD28 engagement mediated slightly greater secretion of IL-10 and IL-22 by ICOS+CD161+CD4+ than by ICOS−CD161+CD4+ T cells. Further, CD28 engagement induced IL-4 secretion by ICOS−CD161+CD4+ T cells. Notably, ICOS but not CD28 engagement promoted the sustained expansion of ICOS+CD161+CD4+ T cells, as indicated via their greater frequency and overall yields (FIG. 6C).

Figure 12:
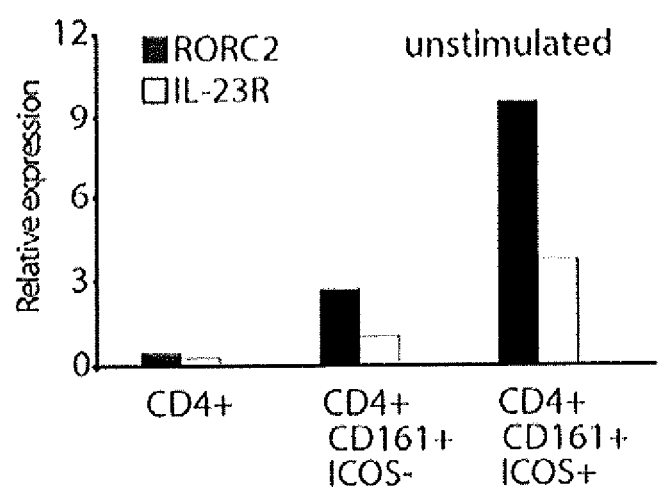
FIG. 12 is an image demonstrating that ICOS+CD161+CD4+ T cells from UCB constitutively express RORC2 and IL23R. CD4+, ICOS+CD161+CD4+ and ICOS-CD161+CD4+ T cells were sorted and their mRNA expression level of RORC2 and IL-23R relative to β-actin was measured by RT-PCR.

It has been reported that CD161+CD4+ T cells constitutively express RORC2 and IL-23R and that Th17-polarizing conditions further up regulate expression of these molecules (Cosmi et al., 2008 J. Exp. Med. 205:1903-1916). Given the results presented herein, it is believed that CD161+CD4+ T cells that constitutively express ICOS would express higher mRNA amounts of RORC2 and IL-23R than ICOS−CD161+CD4+ T cells. Moreover, without wishing to be bound by any particular theory, it is believed that ICOS engagement would further increase RORC2 and IL-23R mRNA expression in ICOS+CD161+CD4+ T cells. Indeed, resting ICOS+CD161+CD4+ UCB T cells expressed higher mRNA amounts of RORC2 and IL-23R than resting ICOS−CD161+CD4+ or bulk UCB T cells (FIG. 12). Furthermore, ICOS engagement induced greater expression of RORC2 and IL-23R mRNA in ICOS+CD161+CD4+ versus ICOS−CD161+CD4+ T cells (FIG. 6D), corresponding with their increased IL-17F and CCL20 secretion (FIG. 6B). In contrast, CD28 engagement induced higher mRNA expression amounts of AHR in ICOS+CD161+CD4+ T cells (FIG. 6D), consistent with their enhanced IL-22 production (FIG. 6B). Thus, in addition to CD161, ICOS might be a surface marker for UCB CD4+ T cells that develop into Th17 cells.

Figure 13:
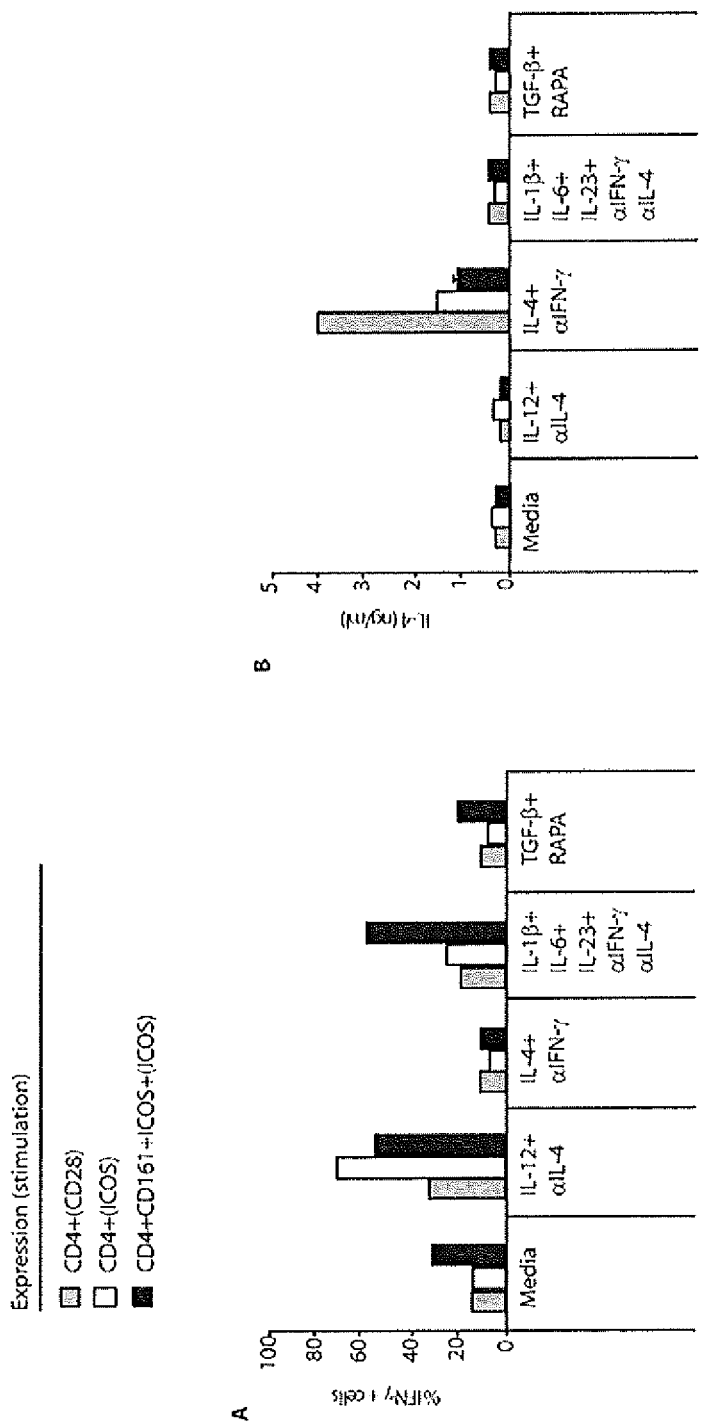
FIG. 13, comprising
Figure 13:
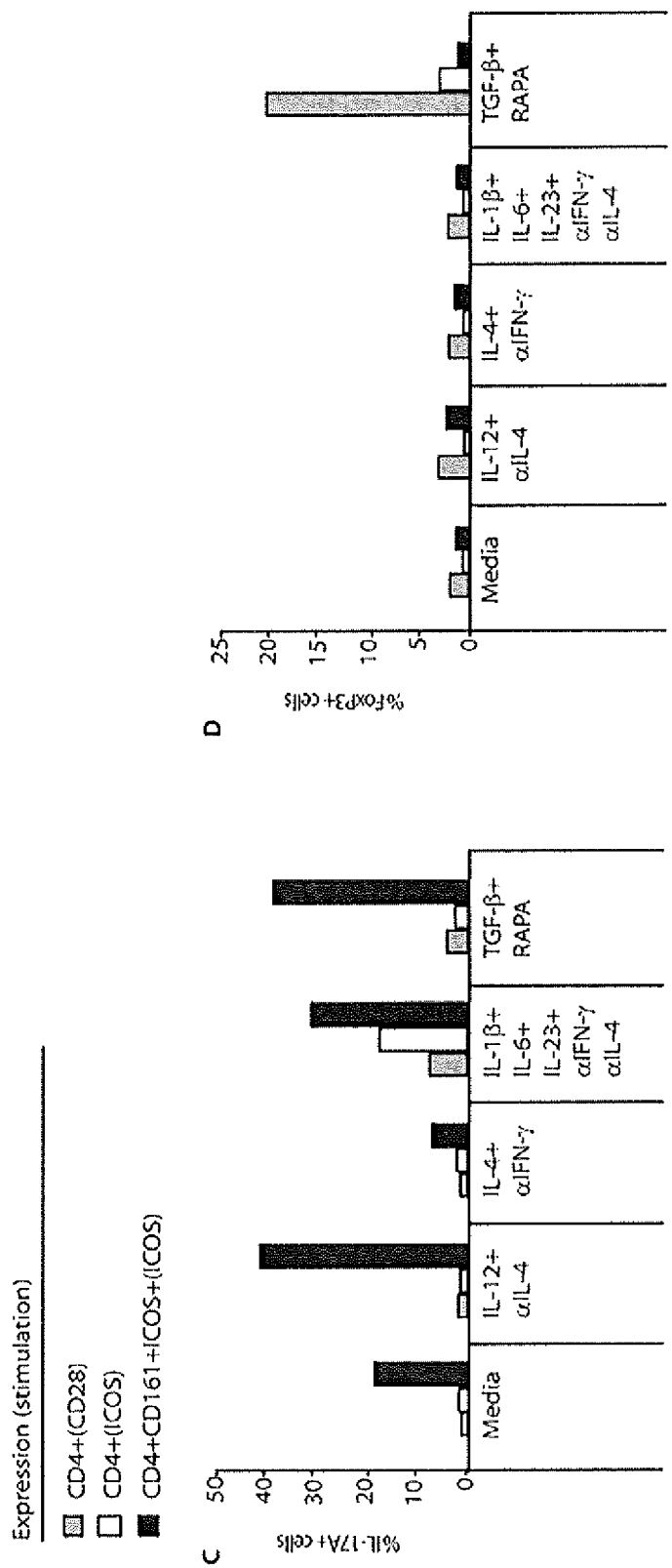

Given that costimulation of ICOS+CD161+CD4+ T cells with ICOS specifically induced RORC2 and IL-17A, it is believed that these cells were imprinted as Th17 cells via the ICOS signal, and consequently, even in the presence of TH1-, TH2-, and Treg-polarizing conditions, these cells would continue to secrete IL-17A and resist differentiation into TH1, TH2, or Treg cells, respectively. To test this notion, ICOS+CD161+CD4+ and ICOS−CD161+CD4+ T cells were sorted and stimulated with antibodies to CD3/CD28- or CD3/ICOS-coated beads, and then cultured in media alone or in TH1-, TH2-, Th17-, and Treg-polarizing conditions. ICOS costimulation of ICOS+CD161+CD4+ T cells induced IL-17A secretion even under TH1-, TH2-, or Treg-polarizing conditions, although at varying amounts (FIG. 6E). In contrast, costimulation through CD28 induced modest amounts of IL-17A secretion, even in the presence of Th17-polarizing conditions (FIG. 6E). Conditions that polarize bulk UCB CD4+ T cells toward a TH1, TH2, Th17, and Treg cell phenotype were effective because they promoted IFN-γ, IL-4, IL-17A secretion, or FoxP3 expression, respectively (FIG. 13). In contrast, ICOS costimulation of ICOS+CD161+CD4+ T cells was unable to elicit IL-4 secretion and failed to promote FoxP3 expression when cultured in conditions that fostered their TH2 or Treg development (FIG. 13). Regardless of the T cell subset-polarizing conditions and the mode of costimulation, it was observed that less than 5% of ICOS−CD161+CD4+ T cells produced IL-17A (FIG. 6E). Thus, the results presented herein indicate that cells with the potential to differentiate into Th17 cells are largely confined to the ICOS+ subset of CD161+CD4+ UCB T cells and are rapidly imprinted as Th17 cells via ICOS signaling.

Example 9: ICOS Augments T Cell-Mediated Tumor Immunity

Figure 7:
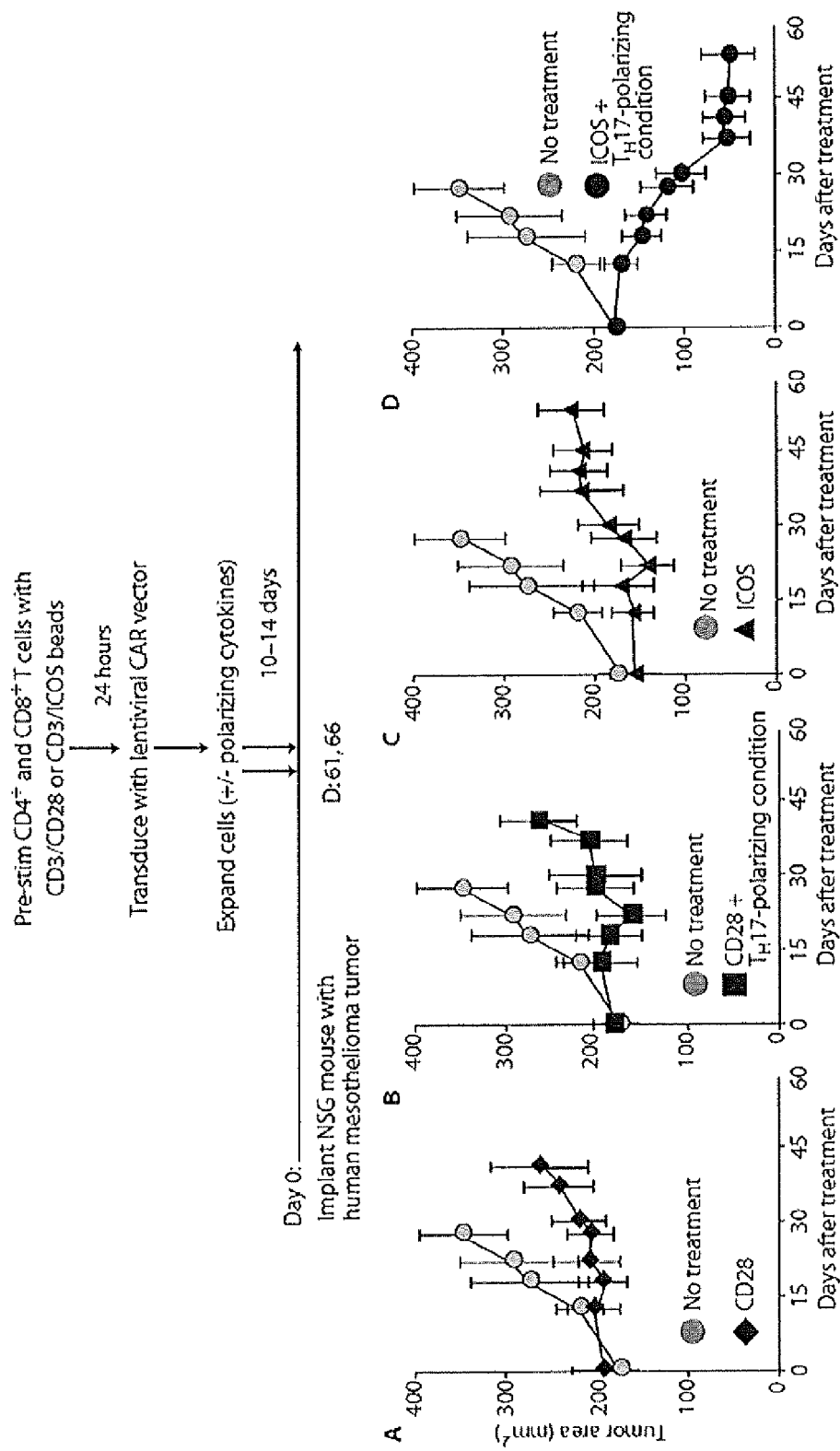
FIG. 7, comprising
Figure 7:
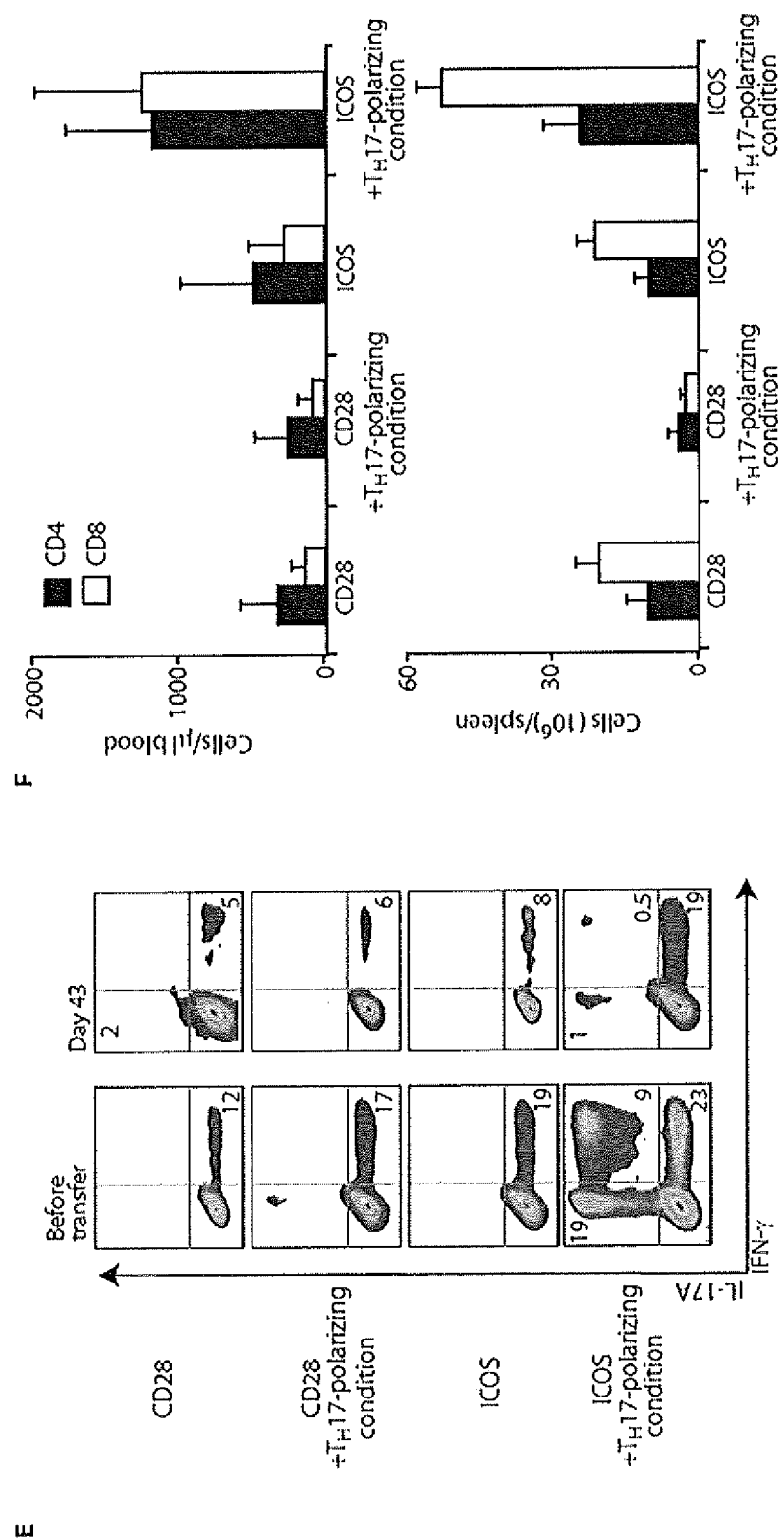

It has been reported that genetically redirected peripheral blood T cells expanded with antibodies to CD3/CD28 beads mediate robust antitumor effects after infusion into mice bearing human tumor xenografts (Carpenito et al., 2009 Proc. Natl. Acad. Sci. U.S.A. 106:3360-3365). Given the present finding that ICOS costimulation in the presence of Th17-polarizing conditions generates IL-17A+IFN-γ+ T lymphocytes in vitro, experiments were designed to investigate how these cells, upon genetic redirection, would affect the growth of human tumors. To test this question, bulk peripheral blood T cells were expanded with antibodies to CD3/CD28 or CD3/ICOS beads in the presence or absence of Th17-polarizing conditions and genetically modified them with a chimeric antigen receptor (CAR) to confer specificity for mesothelin-expressing tumors (FIG. 7 scheme). NOD/scid/IL-2Rgnull mice were injected in the flank with the human mesothelioma cell line M108 and were injected intratumorally with the redirected cells beginning on day 61 after tumor challenge.

It was observed that mice treated with ICOS-stimulated T cells polarized with Th17 cytokines experienced superior tumor regression compared with all other treatment groups (P<0.005; FIG. 7D versus FIGS. 7A to 7C). Only cells stimulated with ICOS in the presence of Th17-polarizing conditions were able to mediate regression of large tumors (FIG. 7D). Cells stimulated by CD28 alone or by CD28 plus Th17-polarizing conditions were able to slow tumor progression, but were unable to mediate long-lasting tumor regression (FIG. 7, A to C). The therapeutic effectiveness of polarized cells stimulated with ICOS may be a consequence of their enhanced IFN-γ secretion upon antigen recognition ex vivo (FIG. 7E) and increased engraftment in vivo (FIG. 7F). The results presented herein identify ICOS and its downstream signaling pathways as a target for the development of cancer immunotherapy to modify Th17 cell function and numbers.

Example 10: The Inducible Costimulator (ICOS) is Critical for the Development of Human Th17 Cells Phylogenetic studies indicate that the co-signaling molecule ICOS arose as a duplication of CD28 and that this event was coincident with the appearance of high-affinity memory antibody responses (Bernard et al., 2007 Immunol. 31:255-271). Although many aspects of the ICOS and CD28 paralogs are conserved, a number of important differences have emerged. For example, the expression pattern of human and mouse CD28 in thymus and peripheral T cells is considerably different (Riley et al., 2005 Blood 105:13-21; Turka et al., 1990 J. Immunol. 144:1646-1653; Gross et al., 1992 J. Immunol. 149:380-388). A difference between ICOS expression in human and mouse CD4+ T cells has been uncovered, where, unlike humans, ICOS is not expressed on recent thymic emigrants in the mouse (Burmeister et al., 2008 J. Immunol. 180:774-782). ICOS-deficient humans have few TFH cells (Bossaller et al., 2006 J. Immunol. 177:4927-4932) and impaired TH1, TH2, and Th17 responses (Takahashi et al., 2009 J. Immunol. 182:5515-5527), suggesting that ICOS signaling has nonredundant roles for the homeostasis of multiple humanCD4+ T cell subsets. The results presented herein suggest that some of these differences between mice and humans could be a result of the earlier expression of ICOS during lymphocyte ontogeny in humans than in mice.

The results presented herein suggest that CD28 and ICOS ligands, in concert with the cytokine milieu, critically dictate the fate of Th17 cells. Previous studies have shown that CD28 costimulation can provide short-term expansion of Th17 cells, and our results are consistent with those findings. However, using an ICOS-based culture system, conditions that permit sustained expansion of human Th17 cells have been identified. Given that ICOSL is constitutively expressed in many tissues, and ICOSL overexpression can result in autoimmunity (Tafuri et al., 2001 Nature 409:105-109; Yu et al., 2007 Nature 450:299-303), the results presented herein raise a question as to how Th17 cell expansion is controlled. The results presented herein may address this paradox in that CD28 ligands temper the growth and inflammatory potential of Th17 cells. These data are particularly interesting in light of recent data describing a new human T cell lineage called TH22 cells, which are characterized by their ability to produce IL-22 but nominal amounts of IL-17A and IFN-γ (Duhen et al., 2009 Nat. Immunol. 10:857-863). The results presented herein suggest that CD28 may transition Th17 cells into TH22 cells, whereas ICOS transitions them into TH1/Th17 cells. The results presented herein support the idea that the fate of T cell subsets, particularly Th17 cells, appears more flexible in humans than previously appreciated (Murphy et al., 2010 Nat. Immunol. 11:674-680).

There are several therapeutic implications from these findings. A number of autoimmune and inflammatory conditions are associated with increased Th17 cells and their associated cytokines. For example, skin lesions in psoriasis show substantial up-regulation of CCL20 and CCR6 (Homey et al., 2000 J. Immunol. 164:6621-6632). In multiple sclerosis, a subset of patients has disease that is dominated by Th17 cells, and this biomarker predicts the lack of response to subsequent therapy with IFN-β (Axtell et al., 2010 Nat. Med. 16:406-412). The relative balance of APCs with ligands for ICOS and CD28 is likely to play a role in the homeostasis of pathogenic and regulatory Th17 cell populations. Thus, modulation of ICOS function may have therapeutic utility in certain autoimmune disorders.

Th17 cells can also promote antitumor immunity in mice and humans (Zou et al., 2010 Nat. Rev. Immunol. 10:248-256; Martin-Orozco et al., 2009 Immunity 31: 787-798; Muranski et al., 2008 Blood 112:362-373). For adoptive therapy, the use of defined cell culture conditions to control CD28 and ICOSL availability may permit the selective growth or depletion of Th17 cells to abrogate chronic inflammation or enhance antitumor immunity, as demonstrated here. ICOS stimulation can be used to generate clinically relevant numbers of human Th17 lymphocytes with potent antitumor activities. New tumor immunotherapy clinical trials are currently being designed on the basis of the findings reported here that will test the antitumor effects of genetically reprogrammed Th17 cells.

Example 11: Pharmaceutical Compositions and Modes of Administration

The following experiments were designed to culture Th17 lymphocytes to obtain extensive in vitro or ex vivo expansion of these cells, while at the same time maintaining Good Manufacturing Practices (GMP) conditions. Under these conditions, it is desirable to culture expand Th17 cells and maintain their function in order to preserve their therapeutic properties.

By applying the presently disclosed concepts and mechanisms relating to the development of Th17 cells, the cells of the invention can be isolated from a biological sample for ex vivo treatment and long-term, culture-expansion. The expanded cells can then be administered to a patient in need thereof for treating a disease. The availability of large numbers of cultured Th17 cells enable more detailed immunological, biochemical, and molecular characterization of these cells. More importantly, because the present methods are adaptable for GMP conditions, clinical testing is feasible, and the cultured Th17 cells may be permitted as a novel form of cell therapy.

The present disclosure also provides pharmaceutical compositions which include a therapeutically effective amount of purified Th17 cells, alone or with a pharmaceutically acceptable carrier. Furthermore, the pharmaceutical compositions or methods of treatment can be administered in combination with other therapeutic treatments, such as chemotherapeutic agents and/or antimicrobial agents, or vaccines.

The amount of purified Th17 cells effective in the treatment of a particular disorder or condition depends on the nature of the disorder or condition, and can be determined by standard clinical techniques. In addition, assays can be employed to identify optimal dosage ranges. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems.

The disclosure also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of immunotherapy comprising administering a T cell to a human patient having a tumor, wherein said T cell is contacted with a first agent that is an anti-CD3 antibody or an anti-CD2 antibody, and a second agent that is an anti-ICOS antibody or ICOS-L, wherein said T cell is contacted with said first and said second agent in the presence of a Th-17 polarizing agent, and wherein said first agent and/or said second agent is attached to a solid phase surface.

2. The method of claim 1, wherein said Th-17 polarizing agent is selected from the group consisting of IL-1β, IL-6, neutralizing anti-IFNγ antibody, anti-IL-4 antibody, and any combination thereof.

3. The method of claim 1, wherein said second agent is an anti-ICOS antibody.

4. The method of claim 1, wherein said T cell is a Th17 cell that has been contacted with an antigen.

5. The method of claim 1, wherein said first agent is an anti-CD3 antibody attached to a solid phase surface, and wherein said second agent is an anti-ICOS antibody attached to a solid surface.

* * * * *